(12) United States Patent
Bisgrove et al.

(10) Patent No.: US 9,127,283 B2
(45) Date of Patent: Sep. 8, 2015

(54) INDUCIBLE EXPRESSION SYSTEM TRANSCRIPTION MODULATORS COMPRISING A DISTRIBUTED PROTEIN TRANSDUCTION DOMAIN AND METHODS FOR USING THE SAME

(75) Inventors: Dwayne Bisgrove, Mountain View, CA (US); Hiroaki Sagawa, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 13 days.

(21) Appl. No.: 13/303,652

(22) Filed: Nov. 23, 2011

(65) Prior Publication Data

US 2012/0129254 A1    May 24, 2012

Related U.S. Application Data

(60) Provisional application No. 61/417,062, filed on Nov. 24, 2010.

(51) Int. Cl.
*C12N 15/09* (2006.01)
*C12N 15/31* (2006.01)
*C12N 15/63* (2006.01)
*C07K 14/47* (2006.01)
*C12N 15/82* (2006.01)

(52) U.S. Cl.
CPC .......... *C12N 15/635* (2013.01); *C07K 14/4703* (2013.01); *C07K 14/4705* (2013.01); *C12N 15/8217* (2013.01); *C12N 15/8238* (2013.01); *C07K 2319/10* (2013.01); *C07K 2319/80* (2013.01); *C07K 2319/81* (2013.01)

(58) Field of Classification Search
None
See application file for complete search history.

(56) References Cited

U.S. PATENT DOCUMENTS

| | | | |
|---|---|---|---|
| 5,464,758 A | 11/1995 | Gossen et al. | |
| 5,589,362 A | 12/1996 | Bujard et al. | |
| 5,650,298 A | 7/1997 | Bujard et al. | |
| 5,654,168 A | 8/1997 | Bujard et al. | |
| 5,789,156 A | 8/1998 | Bujard et al. | |
| 5,859,310 A | 1/1999 | Bujard et al. | |
| 5,866,755 A | 2/1999 | Bujard et al. | |
| 5,888,981 A | 3/1999 | Bujard et al. | |
| 5,912,411 A | 6/1999 | Bujard et al. | |
| 5,922,927 A | 7/1999 | Bujard et al. | |
| 6,004,941 A | 12/1999 | Bujard et al. | |
| 6,252,136 B1 | 6/2001 | Bujard et al. | |
| 6,271,341 B1 | 8/2001 | Baron et al. | |
| 6,271,348 B1 | 8/2001 | Bujard et al. | |
| 6,521,455 B2 | 2/2003 | O'Hare et al. | |
| 6,773,920 B1 | 8/2004 | Dalby et al. | |
| 6,783,756 B2 | 8/2004 | Bujard et al. | |
| 7,371,809 B2 | 5/2008 | Brandt et al. | |
| 7,541,446 B2 | 6/2009 | Hillen et al. | |
| 7,700,754 B1 | 4/2010 | Hiraoka et al. | |
| 2003/0208783 A1 | 11/2003 | Hillen et al. | |
| 2003/0216296 A1 | 11/2003 | Park et al. | |
| 2004/0023391 A1 | 2/2004 | Fang et al. | |
| 2004/0038249 A1 | 2/2004 | Darteil et al. | |
| 2006/0099677 A1 | 5/2006 | Lee et al. | |
| 2006/0229246 A1 | 10/2006 | Hawley-Nelson et al. | |
| 2009/0257985 A1 | 10/2009 | Nelson et al. | |
| 2010/0004165 A1 | 1/2010 | Brophy et al. | |
| 2010/0251392 A1 | 9/2010 | Shen et al. | |
| 2011/0112040 A1 | 5/2011 | Liu et al. | |

FOREIGN PATENT DOCUMENTS

| | | |
|---|---|---|
| WO | WO 99/10376 A1 | 3/1999 |
| WO | 2007130073 A2 | 11/2007 |
| WO | 2008148223 A1 | 12/2008 |
| WO | 2012071549 A2 | 5/2012 |

OTHER PUBLICATIONS

Pooga et al., FASEB Journal, 12, 67-77, 1998.*
Pooga et al., FASEB Journal express article, 10.1096/fj.00-0780fje. Published Online Apr. 18, 2001.*
Fuchs et al., ACS Chem. Biol., 2:167-170, 2007.*
Clontech Laboratories, Inc. 'Tet-Off® and Tet-On® Gene Expression Systems User Manual' Sep. 13, 2005, Protocol No. PT3001-1, Version No. PR58969, pp. 1-55.
Mortlocket et al. 'Suppression of gene expression by a cell-permeable Tet repressor' Nucleic Acids Research, 2003, vol. 31, No. 23 e152, pp. 1-7.
Delisle et al., "Pdx-1 or Pdx-1-VP16 protein transduction induces β-cell gene expression in liver-stem WB cells", BMC Research Notes, vol. 2, No. 1, p. 1 of 8-p. 8 of 8 (2009).
Fuchs et al., "Increasing the potency of a cytotoxin with an argenine graft", Protein Engineering, Design & Selection, vol. 20, No. 10, pp. 505-509 (2007).
Noda et al., "Transduction of MyoD protein into myoblasts induces myogenic differentiation without addition of protein transduction domain", Biochemical and Biophysical Research Communications, vol. 382, No. 2, pp. 473-477 (2009).
Noguchi and Matsumoto, "Protein Transduction Technology: A Novel Therapeutic Perspective", Acta Medica Okayama, vol. 60, No. 1, pp. 1-11 (2006).
Schnappinger et al., "Solvent-exposed Residues in the Tet repressor (TetR) Four-helix Bundle Contribute to Subunit Recognition and Dimer Stability", Journal of Biological Chemistry, vol. 274, No. 10, pp. 6405-6410 (1999).

(Continued)

*Primary Examiner* — Nancy T Vogel
(74) *Attorney, Agent, or Firm* — Otto C. Guedelhoefer, IV; Bret E. Field; Bozicevic, Field & Francis LLP

(57) ABSTRACT

Aspects of the invention include inducible expression systems in which a transcription modulator having a distributed protein transduction domain is employed. Aspects of the invention further include methods of using the systems to induce expression of a coding sequence, as well as kits that find use in practicing methods of the invention. The systems, components thereof, methods and kits find use in a variety of different applications.

21 Claims, 11 Drawing Sheets
(11 of 11 Drawing Sheet(s) Filed in Color)

(56) References Cited

OTHER PUBLICATIONS

"Tet-Express (TM)-Fast, Inducible Expression", Mammalian Expression Systems, pp. 1-4 (2011).

"Tet-Off Advanced Inducible Gene Expression System User Manual", pp. 1-27 (2007).

Chuanying Pan et al., "Reprogramming human fibroblasts using HIV-1 TAT recombinant proteins OCT4, SOX2, KLF4 and c-MYC", Molecular Biology Reports; an International Journal on Molecular and Cellular Biology, 2009, vol. 37, No. 4, pp. 2117-2124.

Ye et al., "Evaluation of Strategies for the Intracellular Delivery of Proteins", Pharmaceutical Research, 2002, vol. 19, No. 9, pp. 1302-1309.

Clontech catalog. XfectTM-Transfect more cells, 2009, pp. 1-2.

Hideki Matsui et al., "Protein transduction by poly-arginine", Folia Pharmacol. Jpn. (Nippon Yakurigaku Zasshi), 2003, vol. 121, pp. 435-439.

Hirofumi Noguchi et al., "Protein Transduction Technology: A Novel Therapeutic Perspective", Acta Media Okayama, 2006, vol. 60, No. 1, pp. 1-11.

Boinpally et al., "Iontophoresis of lecithin vesicles of clyclosporin A", Int. J. Pharm., 2004, vol. 274, pp. 185-190.

Christiaens et al., "Enhancement of polymethacrylate-mediated gene delivery by Penetratin", European Journal of Pharmaceutical Sciences, 2005, vol. 24, pp. 525-537.

Doyle et al., "Differential intracellular distribution of DNA complexed with polyethylenimine (PEI) and PEI-polyarginine PTD influences exogenous gene expression within live COS-7 cells", Genetic Vaccines and Therapy, Nov. 26, 2007, vol. 5:11.

Fong et al., "Cationic liposome-mediated uptake of human immunodeficiency virus type 1 Tat protein into cells", Journal of Virological Methods, 1997, vol. 66, pp. 149-157.

Ford et al., "Review: Protein Transduction: an Alternative to Genetic Intervention?" Gene Therapy, 2001, vol. 8, pp. 1-4.

Fretz et al., "Strategies for cytosolic delivery of liposomal macromolecules", International Journal of Pharmaceutics, 2005, vol. 298, pp. 305-309.

Fretz et al., "TAT-Peptide Modified Liposomes: Preparation, Characterization, and Cellular Interaction", Methods in Molecular Biology, 2010, vol. 605, pp. 349-359.

Godin et al., "Mechanism of bacitracin permeation enhancement through the skin and cellular membranes from an ethosomal carrier", Journal of Controlled Release, 2004, vol. 94, pp. 365-379.

Hyndman et al., "HIV-1 Tat protein transduction domain peptide facilitates gene transfer in combination with cationic liposomes", Journal of Controlled Release, 2004, vol. 99, pp. 435-444.

Kalia et al., "Iontophoretic drug delivery", Advanced Drug Delivery Reviews, 2004, vol. 56, pp. 619-658.

Lindgren et al., "Cell-penetrating peptides", TIPS, Mar. 2000, vol. 21, pp. 99-103.

Min, S-H et al., "Gene delivery using a derivative of the protein transduction domain peptide, K-Antp", Biomaterials, 2010, vol. 31, pp. 1858-1864.

Mitragotri, Samir. "Synergistic Effect of Enhancers for Transdermal Drug Delivery", Pharmaceutical Research, 2000, vol. 17(11), pp. 1354-1359.

Pillai et al., "Transdermal iontophoresis of insulin: IV. Influence of chemical enhancers", International Journal of Pharmaceutics, 2004, vol. 269, pp. 109-120.

Schwarze et al., "In vivo protein transduction: intracellular delivery of biologically active proteins, compounds and DNA", TIPS, Feb. 2000, vol. 21, pp. 45-48.

Torchilin et al., "TAT-Liposomes: A Novel Intracellular Drug Carrier", Current Protein and Peptide Science, 2003, vol. 4, pp. 133-140.

Li et al. "In vivo delivery of a XIAP (BIR3-RING) fusion protein containing the protein transduction domain protects against neuronal death induced by seizures", Exp. Neurol., Feb. 2006, vol. 197, No. 2, pp. 301-308. Epub Dec. 5, 2005.

\* cited by examiner

FIG. 1A

MSRLDKSKVINSALELLNEVGIEGLTTRKLAQKLGVEQPTLYWHVKNKRALLDAL
AIEMLDRHHTHFCPLEGESWQDFLRNNAKSFRCALLSHRDGAKVHLGTRPTEKQY
ETLENQLAFLCQQGFSLENALYALSAVGHFTLGCVLEDQEHQVAKEERETPTTDS
MPPLLRQAIELFDHQGAEPAFLFGLELIICGLEKQLKCESGGPKLHNHNHNHNHN
HNEFAAAAAAAAAGTPADALDDFDLDMLPADALDDFDLDMLPADALDDFDLDMLP
G

FIG. 1B

MSRLDKSKVINSALELLNEVGIEGLTTRKLA KLGVEQPTLYWHVKNKRALLDAL
AIEMLDRHHTHFCPLEGESWQDFLRNNAKSFR ALLSHRDGAKVHLGTRPTEKQY
ETLENQL FLCQQGFSL NALYALSAVGHFTLGCVLEDQEHQVAKEERETPTTDS
MPPLLRQAIELFDHQGAEPAFLFGLELII GLEKQLKCESGGPKLHNHNHNHNHN
HNEFAAAAAAAAAGTPADALDDFDLDMLPADALDDFDLDMLPADALDDFDLDMLP
G

| prOF # | Mw | #aa | Iso Pt |
|---|---|---|---|
| 7 | 30.9 | 278 | 4.9 |
| 14 | 30.9 | 276 | 5.4 |
| 16 | 29.8 | 267 | 5.6 |

```
                        SEQUENCE LISTING

<160> NUMBER OF SEQ ID NOS: 18

<210> SEQ ID NO 1
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 1

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Lys Leu His Asn His Asn His Asn His Asn His Asn Glu Phe
    210                 215                 220

Ala Ala Ala Ala Ala Ala Ala Ala Gly Thr Pro Ala Asp Ala Leu
225                 230                 235                 240
```

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 2
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 2

Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Arg
                 20                  25                  30

Lys Leu Gly Val Glu Gln Pro Thr Leu Tyr Trp His Val Lys Asn Lys
             35                  40                  45

Arg Ala Leu Leu Asp Ala Leu Ala Ile Glu Met Leu Asp Arg His His
 50                  55                  60

Thr His Phe Cys Pro Leu Glu Gly Glu Ser Trp Gln Asp Phe Leu Arg
 65                  70                  75                  80

Asn Asn Ala Lys Ser Phe Arg Arg Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Arg Phe Leu Cys Gln Gln Gly Phe Ser Leu Arg
            115                 120                 125

Asn Ala Leu Tyr Ala Leu Ser Ala Val Gly His Phe Thr Leu Gly Cys
130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Arg Gly Leu Glu Lys Gln Leu Lys Cys Glu Ser Gly Gly Pro
            195                 200                 205

Lys Leu His Asn His Asn His Asn His Asn His Asn His Asn Glu Phe
            210                 215                 220

Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 3
<211> LENGTH: 335
<212> TYPE: PRT
<213> ORGANISM: Artificial Sequence

```
<220> FEATURE:
<223> OTHER INFORMATION: synthetic polypeptide

<400> SEQUENCE: 3

Met Ser Arg Leu Asp Lys Ser Lys Val Ile Asn Ser Ala Leu Glu Leu
 1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
                260                 265                 270

Gly Glu Asp Val Ala Met Ala His Ala Asp Ala Leu Asp Asp Phe Asp
            275                 280                 285

Leu Asp Met Leu Gly Asp Gly Asp Ser Pro Gly Pro Gly Phe Thr Pro
        290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 4
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 4

Met Ser Arg Leu Asp Lys Ser Lys Val Ile Asn Ser Ala Leu Glu Leu
```

```
                1               5                  10                 15
Leu Asn Glu Val Gly Ile Glu Gly Leu Thr Thr Arg Lys Leu Ala Gln
                20                 25                 30

Lys Leu Gly Val Glu Gln Pro Thr Leu Tyr Trp His Val Lys Asn Lys
                35                 40                 45

Arg Ala Leu Leu Asp Ala Leu Ala Ile Glu Met Leu Asp Arg His His
    50                 55                 60

Thr His Phe Cys Pro Leu Glu Gly Glu Ser Trp Gln Asp Phe Leu Arg
65                  70                 75                 80

Asn Asn Ala Lys Ser Phe Arg Cys Ala Leu Leu Ser His Arg Asp Gly
                85                 90                 95

Ala Lys Val His Leu Gly Thr Arg Pro Thr Glu Lys Gln Tyr Glu Thr
                100                105                110

Leu Glu Asn Gln Leu Ala Phe Leu Cys Gln Gln Gly Phe Ser Leu Glu
                115                120                125

Asn Ala Leu Tyr Ala Leu Ser Ala Val Gly His Phe Thr Leu Gly Cys
    130                135                140

Val Leu Glu Asp Gln Glu His Gln Val Ala Lys Glu Glu Arg Glu Thr
145                 150                155                160

Pro Thr Thr Asp Ser Met Pro Pro Leu Leu Arg Gln Ala Ile Glu Leu
                165                170                175

Phe Asp His Gln Gly Ala Glu Pro Ala Phe Leu Phe Gly Leu Glu Leu
                180                185                190

Ile Ile Cys Gly Leu Glu Lys Gln Leu Lys Cys Glu Ser Gly Gly Pro
                195                200                205

Ala Asp Ala Leu Asp Asp Phe Asp Leu Asp Met Leu Pro Ala Asp Ala
                210                215                220

Leu Asp Asp Phe Asp Leu Asp Met Leu Pro Ala Asp Ala Leu Asp Asp
225                 230                235                240

Phe Asp Leu Asp Met Leu Pro Gly
                245

<210> SEQ ID NO 5
<211> LENGTH: 335
<212> TYPE: PRT
<213> ORGANISM: Artificial Sequence
<220> FEATURE:
<223> OTHER INFORMATION: synthetic polypeptide

<400> SEQUENCE: 5

Met Ser Arg Leu Asp Lys Ser Lys Val Ile Asn Ser Ala Leu Glu Leu
1               5                  10                 15

Leu Asn Glu Val Gly Ile Glu Gly Leu Thr Thr Arg Lys Leu Ala Gln
                20                 25                 30

Lys Leu Gly Val Glu Gln Pro Thr Leu Tyr Trp His Val Lys Asn Lys
                35                 40                 45

Arg Ala Leu Leu Asp Ala Leu Ala Ile Glu Met Leu Asp Arg His His
    50                 55                 60

Thr His Phe Cys Pro Leu Lys Gly Glu Ser Trp Gln Asp Phe Leu Arg
65                  70                 75                 80

Asn Asn Ala Lys Ser Phe Arg Cys Ala Leu Leu Ser His Arg Asn Gly
                85                 90                 95

Ala Lys Val His Ser Asp Thr Arg Pro Thr Glu Lys Gln Tyr Glu Thr
                100                105                110

Leu Glu Asn Gln Leu Ala Phe Leu Cys Gln Gln Gly Phe Ser Leu Glu
```

```
            115                 120                 125
Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335

<210> SEQ ID NO 6
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 6

Met Ser Arg Leu Asp Lys Ser Lys Val Ile Asn Gly Ala Leu Glu Leu
1               5                   10                  15

Leu Asn Gly Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Pro Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
```

```
                145                 150                 155                 160
Pro Thr Thr Asp Ser Met Pro Pro Leu Leu Arg Gln Ala Ile Glu Leu
                    165                 170                 175

Phe Asp Arg Gln Gly Ala Glu Pro Ala Phe Leu Phe Gly Leu Glu Leu
                    180                 185                 190

Ile Ile Cys Gly Leu Glu Lys Gln Leu Lys Cys Glu Ser Gly Gly Pro
                    195                 200                 205

Ala Asp Ala Leu Asp Asp Phe Asp Leu Asp Met Leu Pro Ala Asp Ala
                    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                    245

<210> SEQ ID NO 7
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 7

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
                    20                  25                  30

Lys Leu Gly Val Glu Gln Pro Thr Leu Tyr Trp His Val Lys Asn Lys
                    35                  40                  45

Arg Ala Leu Leu Asp Ala Leu Pro Ile Glu Met Leu Asp Arg His His
                    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                    85                  90                  95

Ala Lys Val His Leu Gly Thr Arg Pro Thr Glu Lys Gln Tyr Glu Thr
                    100                 105                 110

Leu Glu Asn Gln Leu Ala Phe Leu Cys Gln Gln Gly Phe Ser Leu Glu
                    115                 120                 125

Asn Ala Leu Tyr Ala Leu Ser Ala Val Gly His Phe Thr Leu Gly Cys
                    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                    165                 170                 175

Phe Asp Arg Gln Gly Ala Glu Pro Ala Phe Leu Phe Gly Leu Glu Leu
                    180                 185                 190

Ile Ile Cys Gly Leu Glu Lys Gln Leu Lys Cys Glu Ser Gly Gly Pro
                    195                 200                 205

Thr Asp Ala Leu Asp Asp Phe Asp Leu Asp Met Leu Pro Ala Asp Ala
                    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                    245
```

```
<210> SEQ ID NO 8
<211> LENGTH: 282
<212> TYPE: PRT
<213> ORGANISM: Artificial Sequence
<220> FEATURE:
<223> OTHER INFORMATION: synthetic polypeptide

<400> SEQUENCE: 8
```

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Arg Asn Lys
        35                  40                  45

Gln Thr Leu Met Asn Met Leu Ser Glu Ala Ile Leu Ala Lys His His
    50                  55                  60

Thr Arg Ser Ala Pro Leu Pro Thr Glu Ser Trp Gln Gln Phe Leu Gln
65                  70                  75                  80

Glu Asn Ala Leu Ser Phe Arg Lys Ala Leu Leu Val His Arg Asp Gly
                85                  90                  95

Ala Arg Leu His Ile Gly Thr Ser Pro Thr Pro Pro Gln Phe Glu Gln
            100                 105                 110

Ala Glu Ala Gln Leu Arg Cys Leu Cys Asp Ala Gly Phe Ser Val Glu
        115                 120                 125

Glu Ala Leu Phe Ile Leu Gln Ser Ile Ser His Phe Thr Leu Gly Ala
    130                 135                 140

Val Leu Glu Glu Gln Ala Thr Asn Gln Ile Glu Asn Asn His Val Ile
145                 150                 155                 160

Asp Ala Ala Pro Pro Leu Leu Gln Glu Ala Phe Asn Ile Gln Ala Arg
                165                 170                 175

Thr Ser Ala Glu Met Ala Phe His Phe Gly Leu Lys Ser Leu Ile Phe
            180                 185                 190

Gly Phe Ser Ala Gln Leu Asp Glu Lys Lys His Thr Pro Ile Glu Asp
        195                 200                 205

Gly Asn Lys Pro Lys Lys Lys Arg Lys Leu Ala Val Ser Val Thr Phe
    210                 215                 220

Glu Asp Val Ala Val Leu Phe Thr Arg Asp Glu Trp Lys Lys Leu Asp
225                 230                 235                 240

Leu Ser Gln Arg Ser Leu Tyr Arg Glu Val Met Leu Glu Asn Tyr Ser
                245                 250                 255

Asn Leu Ala Ser Met Ala Gly Phe Leu Phe Thr Lys Pro Lys Val Ile
            260                 265                 270

Ser Leu Leu Gln Gln Gly Glu Asp Pro Trp
        275                 280

```
<210> SEQ ID NO 9
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 9
```

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Arg
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Lys Leu His Asn His Asn His Asn His Asn His Asn Glu Phe
    210                 215                 220

Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 10
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 10

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Arg
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

```
Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
            195                 200                 205

Lys Leu His Asn His Asn His Asn His Asn His Asn Glu Phe
            210                 215                 220

Ala Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
                260                 265                 270

Met Leu Pro Gly
        275

<210> SEQ ID NO 11
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 11

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190
```

```
Ile Ile Arg Gly Leu Glu Lys Gln Leu Lys Cys Glu Ser Gly Gly Pro
        195                 200                 205

Lys Leu His Asn His Asn His Asn His Asn His Asn Glu Phe
210                 215                 220

Ala Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Phe
            245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 12
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 12

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Arg
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Arg Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Arg Gly Leu Glu Lys Gln Leu Lys Cys Glu Ser Gly Gly Pro
        195                 200                 205

Lys Leu His Asn His Asn His Asn His Asn His Asn Glu Phe
210                 215                 220

Ala Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Phe
            245                 250                 255

Asp Leu Asp Met Leu Pro Ala Asp Ala Leu Asp Asp Phe Asp Leu Asp
            260                 265                 270
```

Met Leu Pro Gly
        275

<210> SEQ ID NO 13
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 13

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Arg
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Arg Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Arg Gly Leu Glu Lys Gln Leu Lys Cys Glu Ser Gly Gly Pro
        195                 200                 205

Lys Leu His Asn His Asn His Asn His Asn His Asn Glu Phe
    210                 215                 220

Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 14
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 14

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Arg
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Ser Trp Gln Asp Phe Leu Arg
65                  70                  75                  80

Asn Asn Ala Lys Ser Phe Arg Arg Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Arg Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Arg Gly Leu Glu Lys Gln Leu Lys Cys Glu Ser Gly Gly Pro
        195                 200                 205

Lys Leu His Asn His Asn His Asn His Asn His Asn Glu Phe
    210                 215                 220

Ala Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
            260                 265                 270

Met Leu Pro Gly
        275

<210> SEQ ID NO 15
<211> LENGTH: 276
<212> TYPE: PRT
<213> ORGANISM: Artificial Sequence
<220> FEATURE:
<223> OTHER INFORMATION: synthetic polypeptide

<400> SEQUENCE: 15

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Arg
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Ser Trp Gln Asp Phe Leu Arg
65                  70                  75                  80

Asn Asn Ala Lys Ser Phe Arg Arg Ala Leu Leu Ser His Arg Asp Gly
                85                  90                  95

```
Ala Lys Val His Leu Gly Thr Arg Pro Thr Glu Lys Gln Tyr Glu Thr
            100                 105                 110

Leu Glu Asn Gln Leu Arg Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Arg Gly Leu Glu Lys Gln Leu Lys Cys Glu Ser Gly Gly Pro
        195                 200                 205

Lys Leu His Asn His Asn His Asn His Asn His Asn Glu Phe
    210                 215                 220

Ala Ala Ala Ala Ala Ala Ala Ala Gly Thr Pro Ala Asp Ala Leu
225                 230                 235                 240

Asp Asp Phe Asp Leu Asp Met Leu Pro Ala Asp Ala Leu Asp Asp Phe
                245                 250                 255

Asp Leu Asp Met Leu Pro Ala Asp Ala Leu Asp Asp Phe Asp Leu Asp
                260                 265                 270

Met Leu Pro Gly
        275

<210> SEQ ID NO 16
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 16

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175
```

-continued

```
Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
        210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
            245

<210> SEQ ID NO 17
<211> LENGTH: 248
<212> TYPE: PRT
<213> ORGANISM: Artificial Sequence
<220> FEATURE:
<223> OTHER INFORMATION: synthetic polypeptide

<400> SEQUENCE: 17

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
            85                  90                  95

Ala Lys Val His Leu Gly Thr Arg Pro Thr Glu Lys Gln Tyr Glu Thr
        100                 105                 110

Leu Glu Asn Gln Leu Ala Phe Leu Cys Gln Gln Gly Phe Ser Leu Arg
    115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
            165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
        210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
            245

<210> SEQ ID NO 18
<211> LENGTH: 267
<212> TYPE: PRT
<213> ORGANISM: Artificial Sequence
```

```
<220> FEATURE:
<223> OTHER INFORMATION: synthetic polypeptide

<400> SEQUENCE: 18

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Lys Leu His Asn His Asn His Asn His Asn His Asn Glu Phe
        210                 215                 220

Ala Ala Ala Ala Ala Ala Ala Ala Gly Thr Gly Ala Ser Met Gln
225                 230                 235                 240

Lys Leu Ile Ser Glu Glu Asp Leu Gly Tyr Pro Tyr Asp Val Pro Asp
                245                 250                 255

Tyr Ala Gly Asp Tyr Lys Asp Asp Asp Lys
                260                 265
```

US 9,127,283 B2

INDUCIBLE EXPRESSION SYSTEM TRANSCRIPTION MODULATORS COMPRISING A DISTRIBUTED PROTEIN TRANSDUCTION DOMAIN AND METHODS FOR USING THE SAME

CROSS REFERENCE TO RELATED APPLICATIONS

Pursuant to 35 U.S.C. §119 (e), this application claims priority to the filing date of the U.S. Provisional Patent Application Ser. No. 61/417,062, filed Nov. 24, 2010; the disclosure of which is herein incorporated by reference.

INTRODUCTION

The ability to reversibly turn genes on and off has great utility for the analysis of gene expression and function, particularly for those genes whose products are toxic to the cell. A number of inducible systems endogenous to mammalian cells involving regulation by heavy-metals, steroid hormones, and heat shock protein are widely used in inducible expression system. However, a major limitation of these inducible mammalian promoters is the pleiotropic effects of the inducers.

Two major types of prokaryotic derived systems have been successfully exploited for regulation of gene expression in a variety of different cells, where these types of systems are the Lac-based systems and the Tet-based systems. Both types of systems are repressor/operator based-systems and derive key elements from their corresponding prokaryotic operon—the E. coli lactose operon for lac, and the transposon Tn10 tetracycline operon for tet.

Tet based systems have been broadly adopted and are widely acknowledged as the method of choice in experiments requiring inducible expression of genes of interest. In its originally reported form, the system employs two plasmids, one expressing the transactivator, e.g., a tTA or rtTA domain fused to a VP16 domain; and the other having an inducible expression cassette comprising a coding sequence operably linked to a promoter and a transactivator responsive element. Establishing a cell line with this two plasmid system involves a two step process. In the first step, a cell line stably expressing the transactivator is established and identified by clonal selection and expression analysis through transient transfection with a transactivator responsive reporter construct. In the second step, the inducible expression cassette comprising the coding sequence of interest is introduced into the cell line made in the previous step and a second round of selection is performed to identify clones displaying transactivator-responsible inducibility of the expression of the coding sequence.

The tet-based inducible expression system has effectively overcome several drawbacks seen in earlier systems which showed high basal levels of expression, poor responsiveness and toxicity of the inducing agent. Such systems are able to achieve induction of coding sequence expression over ranges of several orders of magnitude in a graded manner, responsive to varying levels of an expression mediator. Furthermore, such systems are extremely versatile and amenable to several types of modifications, permitting the study of the role of a particular gene, or combinations thereof, in a wide variety of cell types of interest. Such systems are amenable to use in medical applications including gene therapy protocols and pharmacological small molecule screening. The versatility of such systems has enabled adaptation to situations requiring inducible gene expression in a tissue specific or generalized manner in animal or plant models, opening new avenues to study gene function in vivo.

SUMMARY

Aspects of the invention include inducible expression systems in which a transcription modulator having a distributed protein transduction domain is employed. Aspects of the invention further include methods of using the systems to induce expression of a coding sequence as well as kits that find use in practicing methods of the invention. The systems, components thereof, methods and kits find use in a variety of different applications.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A and 1B provide the protein sequences of prOF7 (SEQ ID NO:1) and prOF14 (SEQ ID NO:2) (Tet Express). The TetR DNA binding domain (the transcription modulator domain) is indicated in grey, the 6×HN region is in yellow, the 9×Ala spacer is in green and the 3×VP16 domain (the expression modulatory domain) is in blue. The locations of the mutations in prOF14 are indicated in red.

DETAILED DESCRIPTION

Figure 2:
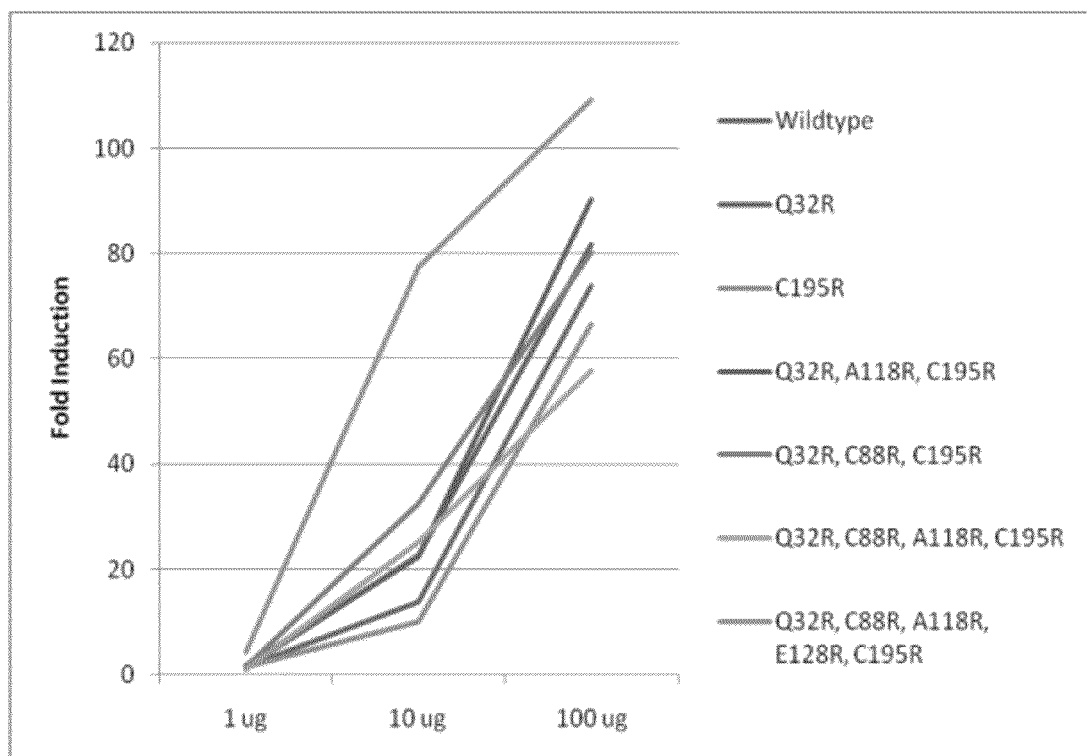
FIG. 2 illustrations the results of a luciferase assay comparing the induction caused by various prOF mutants. The reporter cell line was a HeLa based stable cell line which co-expresses ZsGreen and firefly luciferase under the control of a bidirectional TREtight promoter (Clontech) (hereafter referred to as "clone 19"). Luciferase measurements were taken after an 18 hour exposure to prOF proteins. Fold induction refers to fold over no added protein.

Aspects of the invention include inducible expression systems in which a transcription modulator having a distributed protein transduction domain is employed. Aspects of the invention further include methods of using the systems to induce expression of a coding sequence as well as kits that find use in practicing methods of the invention. The systems, components thereof, methods and kits find use in a variety of different applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Inducible Expression Systems

As summarized above, aspects of the invention include inducible expression systems. By "inducible expression system" is meant all of the components required to perform an inducible expression protocol, i.e., a protocol in which expression of a coding sequence of a cell occurs in response to an applied stimulus, e.g., contact with an expression mediator compound, as compared to a constitutive expression protocol, i.e. a protocol in which expression of a coding sequence in a cell is continuous irrespective of the presence or absence of a particular expression mediator component.

Inducible expression systems of the invention are those that include a transcription modulator and a transcription modulator responsive element, where the transcription modulator binds to the transcription modulator responsive element (in some instances in the presence of an expression mediator) to controllably induce expression of a coding sequence, as desired. Aspects of the invention include transcription modulators that comprise a distributed protein transduction domain (PTD), as described in greater detail below. In some instances, the inducible expression system is based on a prokaryotic operon, e.g., the lac operon, transposon Tn10, tetracycline operon, and the like. In some instances, the inducible expression system is based on a eukaryotic signaling pathway, e.g. steroid receptor-based expression systems, e.g. the estrogen receptor or progesterone-based expression system, the metallothionein-based expression system; the ecdysone-based expression system, As such, transcription modulators and transcription modulator responsive elements may be derived from a variety of different wild-type systems. For convenience of description only, the invention is now further described primarily in terms of Tet-based systems, i.e., systems in which the transcription modulator and transcription modulator responsive element are derived from components of the transposon Tn10 tetracycline operon. However, the invention is not so limited, as the invention is readily applicable to transcription modulators and transcription modulator responsive elements derived from any prokaryotic system e.g. lac-response element, tet response element, or the like; any eukaryotic system, e.g. steroid response element, serum response element, heat shock response element, metallothionein response element, transcription factor binding domain, or the like; or viral system, e.g. the HIV Rev response system.

In certain embodiments, inducible expression systems of the invention include: (a) a host cell that comprises an inducible expression cassette which is responsive to a transcription modulator; (b) a transcription modulator that includes a distributed protein transduction domain; and (c) an expression mediator. The disparate components are configured such that, during use (e.g., in methods as described in greater detail below) inducible expression of a coding sequence (e.g., a gene of interest, inhibitor RNA, other non-protein coding RNAs etc.) is obtained. Each of these components is now described in greater detail below.

Host Cells

Host cells that find use in various embodiments of the invention are those cells which include an inducible expression cassette which is responsive to the transcription modulator of the systems (described in greater detail below). The inducible expression cassette may be chromosomally integrated or episomally maintained in the cell, as desired. When chromosomally integrated, the expression cassette in stably part of a chromosome of the host cell. When episomally maintained, the expression cassette is present on a vector, e.g., a plasmid, an artificial chromosome, e.g. BAC, that is not part of a host cell's chromosome. While the length of the inducible expression cassette may vary, in some instances the length ranges from 0.1 kb to 150 kb, such as 1 to 10 kb and including 5 to 10 kb.

Inducible expression cassettes of interest include a transcription modulator responsive promoter operably linked to a coding sequence. Transcription modulator responsive promoters of inducible expression cassettes of interest include both a transcription modulator responsive element and a minimal promoter element which are operably linked to each other, where the transcription modulator responsive element may be either upstream or downstream from the minimal promoter element, depending on the particular configuration of the expression cassette. Of interest as transcription modulator responsive elements are prokaryotic operon operator sequences, e.g., tet operator sequences. In some instances, the transcription modulator responsive element comprises at least one tet operator sequence. In one embodiment, a transcription modulator responsive element includes multiple copies (e.g., multimerized or concatemerized copies) of 2 or more tet operator sequences. In one configuration of interest, the tet operator sequence(s) is operatively linked upstream (i.e., 5') of the minimal promoter sequence through a phosphodiester bond at a suitable distance to allow for transcription of the target nucleotide sequence upon binding of a regulatory protein (e.g., the regulatory fusion protein) to the tet operator sequence. While the length of the transcription modulator responsive element may vary, in some instances the length of this element ranges from 5 to 1000 base pairs, such as 10 to 100 base pairs, including 15 to 35 base pairs. Specific tet operator sequences of interest include, but are not limited to, those found in the following tet transcription modulator responsive promoters: the $P_{TRE}$ promoter, the $P_{TRE\text{-}Tight}$ promoter, and the $P_{TREG3}$ promoter, all available from Clontech Laboratories, Mountain View, Calif.

As summarized above, the transcription modulator responsive promoter further includes a minimal promoter element operably linked to the transcription modulator responsive element. Minimal promoter sequences of interest are sequences which are not themselves transcribed but which serve (at least in part) to position the transcriptional machinery for transcription. The term "minimal promoter" includes partial promoter sequences which define the start site of transcription for a linked coding sequence to be transcribed but which by themselves are not capable of initiating transcription efficiently, if at all. Thus, the activity of such a minimal promoter is dependent upon the binding of a transcription modulator (e.g., a transcription modulator protein as described below) to an operatively linked transcription modulator responsive element (such as one or more tet operator sequences). Minimal promoters of interest include, but are not limited to: the minimal promoter from the human cytomegalovirus (e.g., nucleotide positions between +75 to −53, nucleotide positions between +75 to −31, etc.); the human HSV thymidine kinase promoter; the human U6 promoter and the like. Promoters of interest include those described, e.g., in Gossen, M. and Bujard, H. (1992) Proc. Natl. Acad. Sci. USA 89:5547-5551. While the length of the minimal promoter element may vary, in some instances the length of this element ranges from 25 to 1000, such as 50 to 100 base pairs.

In some instances, the tet responsive element and the minimal promoter may be separated by a linker sequence, which may be any convenient sequence. In such embodiments, the distance between the transcription modulator responsive element (e.g., the tet operator sequence(s)) and the minimal promoter may vary, and in some instances the tet operator sequence(s) is located within 500 base pairs, such as 400 base pairs, including 300 base pairs, e.g., 200 base pairs, upstream of the minimal promoter.

Specific transcription modulator responsive promoter configurations of interest include, but are not limited to: a cytomegalovirus minimal promoter linked to ten tet operator sequences, a herpes simplex virus minimal tk promoter linked to ten tet operator sequences, etc. Specific transcription modulator responsive promoters of interest include those found in the following commercially available products: the $P_{TRE}$ promoter, the $P_{TRE\text{-}Tight}$ promoter, and the $P_{TREG3}$ promoter, all available from Clontech Laboratories, Mountain View, Calif.

As summarized above, the transcription modulator responsive promoter element is operably linked to a coding sequence, such that upon binding of the transcription modulator to the transcription modulator responsive element, the coding sequence is expressed. The coding sequence of the inducible expression cassette can encode a protein of interest or a nucleic acid of interest (e.g., an inhibitory RNA). Thus, upon induction of transcription of the coding sequence of the expression cassette and translation of the resultant mRNA, in certain embodiments the protein of interest is produced in a host cell or animal. Alternatively, the coding sequence to be transcribed can encode for an active RNA molecule, e.g., an antisense RNA, sRNA, ribozyme, miRNA, etc. Expression of active RNA molecules in a host cell or animal can be used to regulate functions within the host (e.g., prevent the production of a protein of interest by inhibiting translation of the mRNA encoding the protein). While the length of the coding sequence may vary, in some instances the coding sequence has a length ranging from 10 bp to 15,000 bp, such as 50 bp to 5,000 bp and including 100 bp to 1000 bp.

The coding sequence of the inducible expression cassette may be exogenous or endogenous. An "exogenous" coding sequence is a nucleotide sequence which is introduced into the host cell, e.g., into the genome of the host. The exogenous coding sequence may not be present elsewhere in the genome of the host (e.g., a foreign nucleotide sequence) or may be an additional copy of a sequence which is present within the genome of the host but which is integrated at a different site in the genome. An "endogenous" coding sequence is a nucleotide sequence which is present within the genome of the host. An endogenous gene can be operatively linked to an operator sequence(s) to produce an inducible expression cassette of the invention by homologous recombination between an operator sequence recombination vector and sequences of the endogenous gene, such that the native promoter is replaced with the regulatory protein responsive element and the endogenous gene becomes part of an inducible expression cassette.

The host cell that includes the inducible expression cassette may vary greatly. Host cells may be single cells, cell lines or components of a multi-cellular organism. In some instances, the cell is a eukaryotic cell. Some examples of specific cell types of interest include, but are not limited to: bacteria, yeast (e.g., *S. cerevisiae, S. pombe, P. pastoris, K. lactis, H. polymorpha*); fungal, plant and animal cells. Host cells of interest include animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The host cells may be prepared using any convenient protocol, where the protocol may vary depending on nature of the target cell, the location of the target cell, e.g., in vitro or in vivo, etc. Where desired, vectors, such as viral vectors, may be employed to engineer the cell to contain the inducible expression cassette, as desired (see e.g., retroviral and adenoviral vectors, such as provided commercially by Clontech Laboratories, Mountain View, Calif.). Depending on the nature of the host cell and/or expression construct, protocols of interest may include electroporation, particle gun technology, calcium phosphate precipitation, transfection agent mediated introduction, direct microinjection, viral infection and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. After the vector nucleic acids comprising the inducible expression cassette of interest have been introduced into a cell, the cell may be incubated, normally at 37° C., sometimes under selection, for a period of about 1-24 hours. Where long-term maintenance of the expression cassette in the host cell is desired, stable integration protocols may be used.

As desired, host cells may be engineered in vitro or in vivo. For host cells that are engineered in vitro, such cells may ultimately be introduced into a host organism. Depending upon the nature of the cells, the cells may be introduced into a host organism, e.g. a mammal, in a wide variety of ways. Hematopoietic cells may be administered by injection into the vascular system, there being $10^4$ or more cells and in some instances $10^{10}$ or fewer cells, such as $10^8$ or fewer cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the burn or other lesion. For myoblasts or fibroblasts, the number of cells may be $10^4$ or greater and and in some instances $10^8$ or less, where the cells may be applied as a dispersion, generally being injected at or near the site of interest. The cells may be in a physiologically-acceptable medium.

Transcription Modulator

As summarized above, another component of the systems of the invention is a transcription modulator (also referred to as a regulatory protein). Transcriptional modulators of interest are configured to modulate, e.g., induce or repress, expression of the inducible expression cassette in the host cell, e.g., as described above, by binding to a responsive element of the inducible expression cassette, e.g., as described above. While the sequence of transcription modulators of interest may vary, in some instances the sequences include between 5 and 5,000, such as 100 to 700 amino acid residues. Transcription modulators of embodiments of the invention are fusion proteins that include a transcription modulator (i.e., regulatory) domain, an expression modulating domain and a distributed protein transduction domain. Each of these components of the transcription modulators is now described in greater detail below.

The transcription modulator (i.e., regulatory) domain is a domain that binds to the transcription modulator responsive element of the inducible expression cassette. The transcription modulator domain may be configured to bind to the responsive element in either the presence of or the absence of an expression mediator. An expression mediator is a compound that binds to the transcription modulator, e.g., at a mediator binding domain of the transcription modulators, and, in doing so, mediates whether the transcription modulator binds to the transcription modulator responsive element or not. In some instances the transcription modulator domain is one that binds to the responsive element in the presence of the expression mediator, but not in the absence of the expression mediator. Alternatively, in some instances the transcription modulator domain is one that binds to the responsive element in the absence of the expression mediator, but not in the presence of the expression mediator. While the length of the transcription modulator domain may vary, in some instances the transcription modulator domain ranges in length from 5 to 1,000 amino acids, such as 5 to 500 amino acid, and including 5 to 15 amino acid residues.

Of interest as transcription modulator domains are tet-based transcription modulator domains, which modulator domains include one or more TetR domains, i.e., domains that are found in or derived from domains found in a wild-type TetR protein.

For example, in certain embodiments where the transcription modulator binds to the responsive element in the absence of the expression mediator, the transcription modulator domain may be a domain found in a wild-type Tet repressor (which binds to a tet operator sequence(s) in the absence but not the presence of an expression mediator, such as tetracycline). A variety of different wild-type Tet repressors of different classes may be used as a source of the transcription modulator domain, where wild-type Tet repressor classes of interest include, but are not limited to: TetR(A) class, e.g., the Tet repressor carried on the Tn1721 transposon (Allmeir et al. (1992) Gene 111(1): 11-20; NCBI (National Library of Medicine, National Center for Biotechnology Information) accession number X61367 and database cross reference number (GI:) for encoded protein sequence GI:48198); the TetR(B) class, e.g., the Tet repressor encoded by a Tn10 tetracycline resistance determinant (Postle et al. (1984) Nucleic Acids Research 12(12): 4849-63, Accession No. X00694, GI:43052); the TetR(C) class, e.g., the tetracycline repressor of the plasmid pSC101 (Brow et al. (1985) Mol. Biol. Evol. 2(1): 1-12, Accession No. M36272, GI: 150496); the TetR(D) class, e.g., the Tet repressor identified in Salmonella ordonez (Allard et al. (1993) Mol. Gen. Genet. 237(1-2): 301-5, Accession No. X65876, GI:49075); the TetR(E) class, e.g., the Tet repressor isolated from a member of Enterobacteriaceae (Tovar et al. (1988) Mol. Gen. Genet. 215(1): 76-80, Accession No. M34933, GI:155020); the TetR(G) class, e.g., the Tet repressor identified in Vibrio anguillarum (Zhao et al. (1992) Microbiol Immunol 36(10): 1051-60, Accession No. S52438, GI:262929); the TetR(H) class, e.g., the Tet repressor encoded by plasmid pMV11 isolated from Pasteurella multocida (Hansen et al. (1993) Antimicrob. Agents. Chemother. 37(12): 2699-705, Accession No. U00792, GI:392872); the TetR(J) class, e.g., the Tet repressor cloned from Proteus mirabilis (Magalhaes et al. (1998) Biochim. Biophys. Acta. 1443(1-2): 262-66, Accession No. AF038993, GI:410-4706); the TetR(Z) class, e.g., the Tet repressor encoded by the pAG1 plasmid isolated from the gram-positive organism Corynebacterium glutamicum (Tauch et al. (2000) Plasmid 44(3): 285-91, Accession No. AAD25064, GI:4583400). In certain embodiments, the transcription modulator domain is a class B tet repressor, e.g., a Tn10-derived Tet repressor. Examples of specific transcription modulator domains that bind to a responsive element in the absence of an expression mediator include, but are not limited to, the transcription modulator domains found in the following transcription modulators: the Tet-Off transcription modulator; and the Tet-Off Advanced transcription modulator; both of which are available from Clontech Laboratories, Mountain View, Calif.

As another example, in certain embodiments where the transcription modulator binds to the responsive element in the presence of the expression mediator, the transcription modulator domain may be a domain found in a a mutated Tet repressor domain that only binds to the regulatory responsive element in the presence of the expression mediator. The amino acid difference(s) between a mutated Tet repressor and a wild-type Tet repressor may be substitution of one or more amino acids, deletion of one or more amino acids or addition of one or more amino acids. In some instances, the mutated Tet repressor of the invention has the following functional properties: 1) the polypeptide can bind to a tet operator sequence, i.e., it retains the DNA binding specificity of a wild-type Tet repressor; and 2) it is regulated in a reverse manner by the expression mediator compared to a wild-type Tet repressor, i.e., the mutated Tet repressor binds to a regulatory responsive element only in the presence of an expression mediator rather than in the absence of the expression mediator.

In one embodiment, a mutated Tet repressor transcription modulator domain having the functional properties described above is created by substitution of amino acid residues in the sequence of a wild-type Tet repressor. For example, as described in U.S. Pat. No. 5,789,156, a Tn10-derived Tet repressor having amino acid substitutions at amino acid positions 71, 95, 101 and 102 binds to a regulatory responsive element in the presence of the expression mediator. Other amino acid substitutions, deletions or additions at these or other amino acid positions which retain the desired functional properties of the mutated Tet repressor are within the scope of the methods of the invention. Alternative to the above-described mutations, additional suitable mutated Tet repressors (e.g., having the desired functional properties described above) can be created by mutagenesis of a wild type Tet repressor and selection as described in U.S. Pat. No. 5,789,156 (Example 1). A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay, e.g., which allows for selection of a Tet repressor which binds to a Tet operator sequence only in the presence of a substituted tetracycline compound can be used. For example, a library of mutated nucleic acids in an expression vector can be introduced into an *E. coli* strain in which Tet operator sequences control the expression of a gene encoding a Lac repressor and the Lac repressor controls the expression of a gene encoding a selectable marker (e.g., drug resistance). Binding of a Tet repressor to Tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of tetracycline. A nucleic acid encoding a mutated Tet repressor may be selected using this system based upon the ability of the nucleic acid to induce expression of the selectable marker gene in the bacteria only in the presence of a substituted tetracycline compound.

A mutated Tet repressor e.g., having specific mutations (e.g., at positions 71, 95, 101 and/or 102, as described above) can be created by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector.

Specific examples of transcription modulator domains that induce expression in the presence of an expression mediator include, but are not limited to, the transcription modulator domains found in the following transcription modulators: the Tet-On transcription modulator; and the Tet-On Advanced transcription modulator and the Tet-On 3G transcription modulator; all of which are available from Clontech Laboratories, Mountain View, Calif.

In addition to the transcription modulator domain, the transcription modulator further includes an expression modulatory domain, wherein the expression modulatory domain is operatively linked, e.g., fused, to the transcription modulator domain. The expression modulatory domain is a domain that modulates transcription of the inducible expression cassette, where the modulatory activity may be activation or suppression (i.e., repression) of transcription.

Accordingly, in some instances the expression modulatory domain directly or indirectly activates transcription in eukaryotic cells. In these embodiments, the expression modulatory domain may be referred to as an activation domain, i.e. an expression activation domain. In these embodiments, the activation domain may itself possess transcriptional activation activity (i.e., the domain directly activates transcription). The expression activation domain may also activate transcription by an indirect mechanism, e.g., through recruitment of a transcriptional activation protein to interact with the regulatory protein. Any convenient expression activation domain may be present in the transcriptional modulator. The length of the expression activation domain may vary, ranging in some instances from 5 to 1000, such as 5 to 500, including 5 to 15 amino acids. Expression activation domains of interest include, but are not limited to: the herpes simplex virus virion protein 16 (referred to herein as VP16, the amino acid sequence of which is disclosed in Triezenberg, S. J. et al. (1988) Genes Dev. 2:718-729); acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753-881 of GAL4, amino acid residues 416-550 of NF-κB RelA or multimers of amino acid residues 535-545 of RelA, and amino acid residues 165-252 (the "CAD domain") of CREB. Examples of proline-rich activation domains include amino acid residues 399-499 of CTF/NF1 and amino acid residues 31-76 of AP2. Examples of serine/threonine-rich transcription activation domains include amino acid residues 1-427 of ITF1 and amino acid residues 2-451 of ITF2. Examples of glutamine-rich activation domains include amino acid residues 175-269 of Oct I and amino acid residues 132-243 of Sp1. The amino acid sequences of each of the above described regions, and of other useful transcriptional activation domains, are disclosed in Seipel, K. et al. (EMBO J. (1992) 13:4961-4968).

As mentioned above, in some instances, the expression activation domain may indirectly activate transcription by recruiting a transcriptional activator to interact with regulatory protein. For example, an expression activation domain may be capable of mediating a protein-protein interaction with a transcriptional activator protein, such as an endogenous activator present in a host cell. Examples of such domains include leucine zippers, helix-loop-helix domains and zinc finger domains.

Specific examples of expression activation domains that induce expression in the presence of an expression mediator include, but are not limited to, the expression activation domains found in the following transcriptional modulators: the Tet-off transcription modulator, the Tet-Off Advanced transcription modulator; the Tet-On transcription modulator; and the Tet-On Advanced transcription modulator and the Tet-On 3G transcription modulator; all of which are available from Clontech Laboratories, Mountain View, Calif.

As reviewed above, the expression modulatory domain may also be a domain that directly or indirectly suppresses transcription in eukaryotic cells. In these embodiments, the expression modulatory domain may be referred to as a suppression domain, i.e. expression suppression domain. In these embodiments, the suppression domain may itself possess transcription suppression activity (i.e., the domain directly suppresses transcription). By "suppresses transcription" is meant that transcriptional activity is at least detectably reduced compared to a control situation in which the expression suppression domain is not present, an includes embodiments where it is inhibited to the level that transcription is not detectable. The expression suppression domain may also suppress transcription by an indirect mechanism, e.g., through recruitment of a transcriptional suppression protein to interact with the regulatory protein. Any convenient expression suppression domain may be present in the transcriptional modulator. The length of the expression suppression domain may vary, ranging in some instances from 5 to 1000, such as 5 to 500, including 5 to 100 amino acids. Expression suppression domains of interest include, but are not limited to: suppression domains found in the following transcription suppressors: Kruppel protein, the engrailed protein, the knirps protein, the paired protein and the even-skipped protein, all from *Drosophila*; the SIN3, GAL80, and TUP1 proteins, all from *Saccharomyces cerevisiae*; the tet repressor; the Egr-1, WT1, RARa, KRAB, verbA, YY1, ADE1 B, E4B4, SCI P, kid-1, Znf2, and kox-1 proteins; and the like. In some instances, the domain is a KRAB domain, e.g., as found in various zinc finger proteins, such as Kid1. Of interest in certain embodiments is the repressor domain found in the tTS trasncription modulator from Clontech Laboratories (Mountain View, Calif.).

In addition to the regulatory (i.e., transcription modulator) domain and expression modulatory domain, e.g., as described above, transcription modulators of the invention further include a distributed protein transduction domain, or distributed PTD. By protein transduction is meant the translocation of a protein across the cell membrane of a cell. By protein transduction domain is meant a domain or region of the protein that confers protein transduction capability onto the protein. Accordingly, the protein transduction domain confers onto the transcription modulator the ability to pass into the cytoplasm of a cell from outside of the cell, e.g., from culture medium in which the cell is present. Accordingly, the transcription modulator can pass from cell culture medium outside of a cell through the cell membrane into the cytoplasm of the cell.

The protein transduction domains in transcription modulators of the invention are distributed protein transduction domains. By distributed is meant the amino acids of the protein transduction domain are distributed throughout the polypeptide, rather than sequestered as a discrete domain of consecutive amino acids within the polypeptide. As such protein transduction domain is made up of multiple non-sequential amino acid residues that, upon folding of the protein into a three-dimensional structure, make up a "basic-patch" on the surface of the protein that imparts protein transduction activity to the protein. In other words, the distributed protein transduction domain arises from the interaction of multiple non-sequential residues which, when the protein assumes a tertiary structure, are part of a basic patch. A "basic patch" is a surface region of a folded protein that comprises 3 or more, such as 5 or more, including 10 or more number basic amino acid residues, i.e., histidine (H), lysine (K) or arginine (R). The total number of basic residues in a given basic patch may vary, ranging in some instances from 2 to 50, such as 3 to 30 and including 5 to 20, e.g. 2 or more residues, 3 or more residues, 4 or more residues, 5 or more residues, in some instances 6 or more residues, 8 or more residues, or 10 or more residues, e.g. 20 residues or more. The surface area of the basic patch may vary, ranging in some instances from 5 to 10,000 Å², such as 25 to 100 Å². As the basic patch of the distributed protein transduction domain arises from non-sequential amino acid residues, at least some of the residues that participate in (i.e., are members of) the basic batch are non-sequential in the primary sequence of the protein. As such, two or more residues present in the basic patch of the distributed protein transduction domain may be separated from each other in the primary sequence by a region or domain that is 1 or more residues long, such as 2 or more residues long, including 3 or more residues long, e.g., 4 or more, 5 or more, 10 or more residues long. The number of pairs of residues that participate in the basic patch and are separated in the primary sequence by one or more intervening residues may vary, where the number may be 2 or more, 3 or more, 4 or more, 5 or more, 10 or more, etc. As such, the distributed protein transduction domains are distinguished from "cannonical" protein transduction domains which are made of up sequential residues in the primary sequence of the protein in which that are found. Accordingly, the distributed protein transduction domains may be viewed as non-cannonical protein transduction domains.

In some embodiments, a distributed protein transduction domain may be created in a non-transducing polypeptide, e.g. by substituting neutral or acidic residues that are located on the protein surface when the protein assumes a tertiary structure with basic residues to create a basic residue patch on the protein surface. The distributed protein transduction domain created by these mutations will then promote the transduction of the mutant transcription modulator across the cell membrane. In some embodiments, the transduction of a protein that exhibits some ability to cross the cell membrane may be enhanced by modifying an existing distributed protein transduction domain in the protein, e.g. to modify the size or position of the basic patch on the protein surface. In other words, the transcription modulator is mutated to comprise an enhanced distributed protein transduction domain. Such modifications may enhance the efficiency of protein transduction by 2-fold or more, over an existing distributed protein transduction domain, for example by 3-fold or more, or 4-fold or more, in some instances 5-fold or more, 6-fold or more, 7-fold or more, or 8-fold or more, e.g. 10-fold or more, 15-fold or more, or 20-fold or more. Transduction proteins that include a distributed PTD may be fabricated using any convenient protocol. Nucleic acids encoding a parent transduction protein may be mutated using any convenient protocol to generate targeted changes in the sequence of the encoded protein to provide the desired distributed PTD. The DNA sequence or protein product of such a mutation will usually be substantially similar to the sequences provided herein, e.g., will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), Biotechniques 14:22; Barany (1985), Gene 37:111-23; Colicelli et al. (1985), Mol. Gen. Genet. 199:537-9; and Prentki et al. (1984), Gene 29:303-13. Methods for site specific mutagenesis can be found in Sambrook et al., Molecular Cloning: A Laboratory Manual, CSH Press 1989, pp. 15.3-15.108; Weiner et al. (1993), Gene 126:35-41; Sayers et al. (1992), Biotechniques 13:592-6; Jones and Winistorfer (1992), Biotechniques 12:528-30; Barton et al. (1990), Nucleic Acids Res 18:7349-55; Marotti and Tomich (1989), Gene Anal. Tech. 6:67 70; and Zhu (1989), Anal Biochem 177:120-4. Neutral or acidic residues that may be mutated to create a distributed protein transduction domain or modify an existing protein transduction domain, e.g. to create an enhanced protein transduction domain, may be determined using any convenient method, for example, publicly available 3D protein modeling software such as RaptorX, ESyPred3D, HHpred, Phyre, Phyre2. Likewise, any convenient method may be used to confirm the effect of mutation at these residues to promote or enhance the transduction of a protein can be readily confirmed by any convenient method, e.g. immunohistochemistry assays, expression assays, etc.

In some instances, the transcription modulator may include one or more additional domains in addition to the transcription modulator domain, the expression activation domain, and the distributed PTD. For example, the transcription modulator may include a protein tag domain, e.g., a tag sequence which serves as a purification tag for the transcription modulator. Any convenient tag sequences may be employed, including but not limited to those described in U.S. Pat. No. 7,176,298 and United States Patent Application Publication No. 20090023898; the disclosures of which are herein incorporated by reference. Specific tag sequences of interest include, but are not limited to: 6×His tags, 6×HN tags, etc. When present, such tags may vary in length, and in some instances range in length from 5 to 500 amino acids, such as 5 to 100 amino acids, including 6 to 12 amino acids. While the tag may be positioned at any convenient location in the transcription modulator, in some instances the tag domain is positioned between the transcription modulator and expression activation domains. Another optional domain of interest is a spacer domain. Spacer domains, when present, may vary in length, ranging in some instances from 2 to 50, such as 5 to 15 amino acids. While the sequence of a spacer domain may be any convenient sequence, in some instances the sequence is a poly-Alanine sequence, a poly glycine sequence, or a mixed amino acid sequence. As with tag domains, spacer domains may be positioned at any convenient location in the transcription modulator, in some instances the tag domain is positioned between the transcription modulator and expression activation domains. One configuration of interest is a transcription modulator domain-tag domain-spacer domain-expression activation domain, e.g., as seen in the prOF7 and prOF14 proteins described in greater detail below.

As reviewed above, in some embodiments the transcription modulator is a tet transcription modulator, such as the Tet-Off, Tet-Off Advanced, Tet-On, Tet-On Advanced, Tet On-3G or tTS transcription modulator (All of which are available from Clontech Laboratories, Mountain View, Calif.). The amino acid sequences for these particular transcription modulators are provided below:

```
Tet Off
                                         (SEQ ID NO: 3)
MSRLDKSKVINSALELLNEVGIEGLTTRKLAQKLGVEQPTLYWHVK
NKRALLDALAIEMLDRHHTHFCPLEGESWQDFLRNNAKSFRCALLS
HRDGAKVHLGTRPTEKQYETLENQLAFLCQQGFSLENALYALSAVG
HFTLGCVLEDQEHQVAKEERETPTTDSMPPLLRQAIELFDHQGAEP
AFLFGLELIICGLEKQLKCESGSAYSRARTKNNYGSTIEGLLDLPD
DDAPEEAGLAAPRLSFLPAGHTRRLSTAPPTDVSLGDELHLDGEDV
AMAHADALDDFDLDMLGDGDSPGPGFTPHDSAPYGALDMADFEFEQ
MFTDALGIDEYGG

Tet Off Advanced
                                         (SEQ ID NO: 4)
MSRLDKSKVINSALELLNEVGIEGLTTRKLAQKLGVEQPTLYWHVK
NKRALLDALAIEMLDRHHTHFCPLEGESWQDFLRNNAKSFRCALLS
```

```
-continued
HRDGAKVHLGTRPTEKQYETLENQLAFLCQQGFSLENALYALSAVG
HFTLGCVLEDQEHQVAKEERETPTTDSMPPLLRQAIELFDHQGAEP
AFLFGLELIICGLEKQLKCESGGPADALDDFDLDMLPADALDDFDL
DMLPADALDDFDLDMLPG Tet On
                                    (SEQ ID NO: 5)
MSRLDKSKVINSALELLNEVGIEGLTTRKLAQKLGVEQPTLYWHVK
NKRALLDALAIEMLDRHHTHFCPLKGESWQDFLRNNAKSFRCALLS
HRNGAKVHSDTRPTEKQYETLENQLAFLCQQGFSLENALYALSAVG
HFTLGCVLEDQEHQVAKEERETPTTDSMPPLLRQAIELFDHQGAEP
AFLFGLELIICGLEKQLKCESGSAYSRARTKNNYGSTIEGLLDLPD
DDAPEEAGLAAPRLSFLPAGHTRRLSTAPPTDVSLGDELHLDGEDV
AMAHADALDDFDLDMLGDGDSPGPGFTPHDSAPYGALDMADFEFEQ
MFTDALGIDEYGG Tet On Advanced
                                    (SEQ ID NO: 6)
MSRLDKSKVINGALELLNGVGIEGLTTRKLAQKLGVEQPTLYWHVK
NKRALLDALPIEMLDRHHTHFCPLEGESWQDFLRNNAKSFRCALLS
HRDGAKVHLGTRPTEKQYETLENQLAFLCQQGFSLENALYALSAVG
HFTLGCVLEEQEHQVAKEERETPTTDSMPPLLRQAIELFDRQGAEP
AFLFGLELIICGLEKQLKCESGGPADALDDFDLDMLPADALDDFDL
DMLPADALDDFDLDMLPG Tet On-3G
                                    (SEQ ID NO: 7)
MSRLDKSKVINSALELLNGVGIEGLTTRKLAQKLGVEQPTLYWHVK
NKRALLDALPIEMLDRHHTHSCPLEGESWQDFLRNNAKSYRCALLS
HRDGAKVHLGTRPTEKQYETLENQLAFLCQQGFSLENALYALSAVG
HFTLGCVLEEQEHQVAKEERETPTTDSMPPLLKQAIELFDRQGAEP
AFLFGLELIICGLEKQLKCESGGPTDALDDFDLDMLPADALDDFDL
DMLPADALDDFDLDMLPG tTS
                                    (SEQ ID NO: 8)
MSRLDKSKVINSALELLNEVGIEGLTTRKLAQKLGVEQPTLYWHVR
NKQTLMNMLSEAILAKHHTRSAPLPTESWQQFLQENALSFRKALLV
HRDGARLHIGTSPTPPQFEQAEAQLRCLCDAGFSVEEALFILQSIS
HFTLGAVLEEQATNQIENNHVIDAAPPLLQEAFNIQARTSAEMAPH
FGLKSLIFGFSAQLDEKKHTPIEDGNKPKKKRKLAVSVTFEDVAVL
FTRDEWKKLDLSQRSLYREVMLENYSNLASMAGFLFTKPKVISLLQ
QGEDPW
```

In some embodiments, the transcription modulator may be a mutant of these particular transcription modulators, e.g., a transcription modulator that has been mutated to include an enhanced PTD. In these instances, the transcription modulator domain may include one or more point mutations as compared to the Tet-Off, Tet-Off Advanced, Tet-On, Tet-On Advanced, Tet On-3G or tTS transcription modulators. Point mutations of interest include, but are not limited to: Q32R, C88R, A118R, E128R, C195R, Q32K, C88K, A118K, E128K, C195K. Of the above specific point mutations, a given tet transcription modulator of the invention may include 1 or more, such as 2 or more, including 3 or more, 4 or more, 5 or more, etc. of the listed point mutations. For purposes of this application, tet regulatory proteins of the invention have an amino acid sequence identity with the amino acid sequence of wild type TetR of 75% or more, such as 80% or more, including 85% or more, including 90% or more.

Expression Mediator

In addition to the host cell and regulatory protein, systems of the invention (depending on the particular embodiment) may further include an expression mediator. Expression mediators of interest are compounds that bind to the transcription modulators, e.g., at a mediator binding domain of the transcription modulators, and, in doing so, mediate whether the transcription modulator binds to the transcription modulator responsive element or not, e.g., as described above. In some embodiments, expression mediators of interest are small molecule compounds, e.g., compounds having a molecular weight of 1000 daltons or less, e.g., 750 daltons or less. Expression mediators of interest include, but are not limited to: tetracyline antibiotics and analogous thereof. In some instances the expression mediator is tetracycline or doxycycline. Also of interest are analogues of the these compounds, e.g., substituted tetracycline compounds as described in published United States Application Publication No. 20090257985. Other mediators of interest include, but are not limited to: ecdysone, RU486, aptamers, antibodies and proteins having mediator functionality.

Methods

Aspects of the invention further include methods of inducing expression in a host cell, where the host cell may be in vitro or in vivo. In practicing methods according to certain embodiments of the invention, the concentration of an expression mediator (e.g., as described above) is changed in a host cell that includes a distributed PTD transcription modulator and an inducible expression cassette responsive thereto in a manner sufficient for expression of the coding sequence of the expression cassette to occur. In other words, the concentration of an expression mediator is increased or decreased in a host cell that includes both a transcription modulator and inducible expression cassette, where the increase or decrease is sufficient to cause the desired coding sequence expression. In some instances, the concentration of expression mediator is increased from substantially zero to an amount sufficient to cause expression of the coding sequence, e.g., in those embodiments where the transcription modulator binds to the responsive element in the presence of the expression mediator. In other embodiments, the concentration of the expression mediator inside of the host cell is decreased to an amount where the transcription modulator causes expression of the coding sequence, e.g., in those embodiments where the transcription modulator binds to the responsive element in the absence of the expression mediator. It is noted that in some instances, an expression mediator is not employed in the methods, e.g., where the transcription modulator binds to the responsive element in the absence of the expression mediator. In these embodiments, such a transcription modulator may be employed without an expression mediator, e.g., by contacting the host cell with the transcription modulator when expression is desired.

The host cell employed in embodiments of the methods of the invention is one that includes both an inducible expression cassette and a sufficient amount of the transcription modulator comprising the distributed PTD. The host cell may be provided in any convenient manner. In some instances, the host cell is provided by transfecting a host cell with a vector comprising a transcription modulator expression cassette and an inducible expression cassette, followed by expression of the coding sequence for the transcription modulator in a manner sufficient to provide requisite amounts of the transcription modulator in the host cell. Any convenient transfection and expression protocols may be employed, including those described in the Tet-Off® and Tet-On® Gene Expression Systems User Manual, Clontech Laboratories, Version No. PR58969 (2006).

Alternatively, the host cell employed in methods of the invention may be provided by contacting the host cell with a suitable amount of the transcription modulator protein under conditions sufficient for the transcription modulator protein to transduce the host cell, i.e., for the transcription modulator protein to be internalized by the host cell. In these embodiments, the host cell is contacted with the transcription modulator protein under transduction conditions. In certain instances, an amount of transcription modulator is contacted with an amount of host cells under cell culture conditions and incubated for a sufficient period of time for transduction to occur. In some instances, an amount of transcription modulator protein ranging from 1 molecule per cell to $1 \times 10E^{12}$ molecules per cell, such as $7 \times 10E^7$ molecules per cell to $7 \times 10E^8$ molecules per cell is contacted with an amount of host cells ranging from 1 to 50 million, such as 10,000 to 100,000 cells. Any convenient culture medium may be employed, where culture media of interest include, but are not limited to: RPMI, DMEM, OptiMEM and the like. The cells and transcription modulator may be incubated for varying amounts of time, e.g., from 5 minutes to 5 days, such as 1 to 4 hours, at various temperatures, e.g., ranging from 4 to 42, such as 30 to 37° C. As such, according to certain embodiments, the methods include a step of transducing a host cell with a transcription modulator that includes a distributed protein transduction domain, e.g., as described above.

In certain of these embodiments, the host cell may be contacted with the transcription modulator in the presence of a transduction enhancer. Transduction enhancers are chemicals that enhance transduction, e.g., by 2 fold or more, e.g., 3 fold or more, including 5 or 10 fold or more. Of interest as transduction enhancers are nucleic acid transfection reagents, where nucleic acid transfection reagents of interest include, but are not limited to: Xfect™ transfection reagent from Clontech Laboratories, Lipofectamine LTX transfection reagent from Life Technologies, Lipofectamine 2000 transfection reagent from Life Technologies, SiQuest transfection reagent from Mirus, Transit-siQuest transfection reagent, Transit-TKO transfection reagent, Transit-LTI transfection reagent, Transit-Jurkat transfection reagent, Transit-2020 transfection reagent; chloroquine, PEG, etc. When employed, the transduction enhancer may be included in the culture medium at any convenient concentration, where in some instances concentrations range from 0.001 mg/mL to 0.1 mg/mL, such as 0.0025 to 0.036 mg/mL and including 0.001 to 0.01 mg/mL.

Following provision of the host cell that includes both the transcription modulator and the inducible expression cassette, in those embodiments where an expression mediator is employed, the concentration of an expression mediator in the host cell is changed, e.g., raised or lowered, in an amount sufficient to cause transcription of the coding sequence in the expression cassette. As such, the amount of expression mediator in the host cell is raised or lowered to cause expression of the coding sequence, as desired.

In those instances where the concentration of the expression mediator is increased in the host cell, the host cell may be contacted with a suitable amount of the expression mediator. To induce gene expression in a host cell in vitro, the host cell is contacted with the expression mediator by culturing the cell in a medium containing the expression mediator. When culturing cells in vitro in the presence of the expression mediator, the concentration of the expression mediator may vary, and ranges in some instances from 10 to 1000 ng/ml. The expression mediator can be directly added to media in which cells are already being cultured, or cells can be harvested from expression mediator-free media and cultured in fresh media containing the desired expression mediator. To induce gene expression in vivo, host cells within in a subject are contacted with the expression mediator by administering the expression mediator to the subject. In one embodiment, when the expression mediator is administered to a human or animal subject, the dosage is adjusted to achieve a serum concentration ranging from 0.0005 and 1.0 µg/ml. The expression mediator can be administered to a subject by any means effective for achieving an in vivo concentration sufficient for gene induction. Examples of suitable modes of administration include oral administration (e.g., dissolving the expression mediator in the drinking water), slow release pellets and implantation of a diffusion pump. To administer the expression mediator of the invention to a transgenic plant, the inducing agent can be dissolved in water administered to the plant.

In those embodiments where the concentration of the expression mediator is changed by decreasing the concentrating of the expression mediator, the reverse of the above protocols may be employed. For example, the host cells may be ones that have been maintained in a media containing an amount of expression mediator sufficient to inhibit expression of the coding sequence. In such instances, expression of the coding sequence is induced by harvesting the host cells and culturing them in fresh medium that is free of the expression mediator. For in vitro embodiments, the animal or plant may be one that has been administered the expression mediator, e.g., as described above, and administration of the expression mediator is stopped in order to induce expression of the coding sequence, as desired.

In some instances, following the desired amount of expression of the coding sequence, expression may be stopped by changing the concentration of the expression mediator back to a level that it was at prior to induction of expression.

Where desired, any of the above steps may be repeated, e.g., to achieve the desired amount of expression.

Utility

Methods and compositions of the invention find use in a variety of different applications where it is desirable to be able to turn gene expression on and off, or regulate the level of gene expression, in a rapid, efficient and controlled manner without causing pleiotropic effects or cytotoxicity. Methods and compositions of the invention find use in both in vitro and in vivo applications. Applications in which the methods and compositions find use include, but are not limited to: the study of cellular development and differentiation in eukaryotic cells, plants and animals; in vitro protein production; in vivo protein production; imaging of regulated gene expression in vivo; animal models of human disease; production of stable cell lines; expression of inhibitor RNA; drug screening, gene therapy; etc. Applications of interest include, but are not limited to: those described in Freundlieb, "The Tet System: Powerful, Inducible Gene Expression-The first fifteen years of an ongoing success story," Clontechniques (October 2007).

Applications in which the methods and compositions of the invention find use are further described in U.S. Pat. Nos. 5,888,981; 5,866,755; 5,789,156; 5,654,168; 5,650,298; 6,004,941; 6,271,348; 6,271,341; 6,783,756; 5,464,758; 6,252,136; 5,922,927; 5,912,411; and 5,859,310; as well as United States Published Patent Application No. 20090257985; the disclosures of the specific applications disclosed in these publications being specifically incorporated herein by reference.

Kits

Additional aspects of the invention include kits, e.g., for use in inducible gene expression protocols. In some instances, kits of the invention at least include an amount of a distributed protein transduction domain transcription modulator as described above (or vector sequence encoding the same) and a vector comprising a pro-inducible expression cassette, where the pro-inducible expression cassette comprises a transcription modifier responsive promoter (e.g., as described above) operably linked to a cloning site (e.g., in the form of a restriction site), such as a multiple cloning site (MCS). Additional components that may be present in the kits include, but are not limited to: a transduction enhancing agent, e.g., a DNA transfection reagent; an expression mediator, e.g., tetracycline or dox; a host cell line; a control cell line; etc. The various reagent components of the kits may be present in separate containers, or some or all of them may be pre-combined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information at a removed site.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); nt, nucleotide(s) and the like.

Example 1

Generation of prOF14 (i.e.,"Tet Express")

To develop Tet Express, the Tet-Off® Advanced transcription modulator coding sequence from Clontech was first codon optimized for *E. coli* expression and then cloned into a bacterial expression vector. Next, prOF7 was produced by introducing a 6×HN purification tag (Clontech Laboratories, Mountain View Calif.) followed by a nine alanine linker between the DNA binding domain and the VP16 activation domain as shown in FIG. 1A. When the resultant prOF7 was added to the culture media of a host cell harboring a tet responsive inducible expression cassette, it was observed that the prOF7 protein could by itself transactivate a mammalian reporter cell without the need for a canonical protein transduction domain (PTD) (i.e., a separate and distinct PTD).

Figure 4:
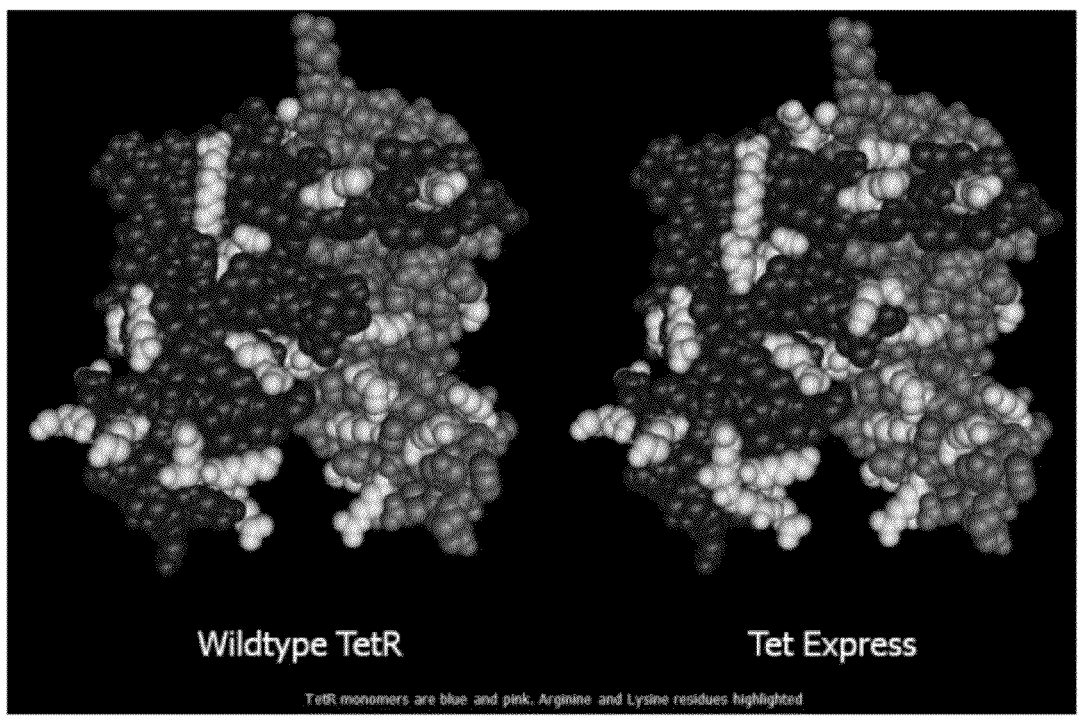
FIG. 4: Mapping the location of arginine and lysine residues in TetR and Tet Express. A prototypical structure of TetR (PDB#2NS7) is shown with the two subunits of the heterodimer colored in pink and blue. The approximate locations of the arginine and lysine residues are indicated in yellow.

The protein sequence of prOF7 was examined and no obvious PTD was identified. It was hypothesized that prOF7 may include a novel distributed PTD such that the distributed PTD is formed by folding of the protein. Clustering of Arg and Lys residues in three-dimensional space could result in a basic patch on the protein surface that could function as a PTD. When lysine and arginine residues were mapped on the structure of tetR, a basic patch was in fact observed. (see FIG. 4).

To determine if the transduction activity of prOF7 could be improved, the basic patch was enlarged by introducing additional arginine residues by point mutation. Fourteen arginine residues were identified which were:

1. Localized to the protein surface,
2. Located near an arg/lys-rich patch
3. Varied between the five different classes of TetR. We favored positions which were arginine in one or more of the other classes.

The 14 arginine residues were introduced in random combinations resulting in 27 different mutant constructs. Mutated proteins were produced as reported in below. Underlining denotes the transcription modulator domain (tetR), italics denotes the expression modulatory domain (VP16), the string of alanines (A) denotes the linker, and bold denotes the arginine substitutions made to improve transduction activity:

```
prOF7
                                              (SEQ ID NO: 1)
MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIICGLEKQLKCESGGPKLHNHNHNHNHNHNEFAAAAAAAAAGT
PADALDDFDLDMLPADALDDFDLDMLPADALDDFDLDMLPG prOF7 + E128R
                                              (SEQ ID NO: 9)
MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLRNALYALSAVGHFT
LGCVLEDQEHQVAKEERETPTTDSMPPLLRQAIELFDHQGAEPAFLF
GLELIICGLEKQLKCESGGPKLHNHNHNHNHNHNEFAAAAAAAAAGT
PADALDDFDLDMLPADALDDFDLDMLPADALDDFDLDMLPG prOF7 + Q32R
                                              (SEQ ID NO: 10)
MSRLDKSKVINSALELLNEVGIEGLTTRKLARKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIICGLEKQLKCESGGPKLHNHNHNHNHNHNEFAAAAAAAAAGT
PADALDDFDLDMLPADALDDFDLDMLPADALDDFDLDMLPG prOF7 + C195R
                                              (SEQ ID NO: 11)
MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAAGT
PADALDDFDLDMLPADALDDFDLDMLPADALDDFDLDMLPG prOF7 + (Q32R, A118R, C195R)
                                              (SEQ ID NO: 12)
MSRLDKSKVINSALELLNEVGIEGLTTRKLARKLGVEQPTLYWHVKN
KRALLDALAIEMLDRHHTHFCPLEGESWQDFLRNNAKSFRCALLSHR
DGAKVHLGTRPTEKQYETLENQLRFLCQQGFSLENALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAAGT
PADALDDFDLDMLPADALDDFDLDMLPADALDDFDLDMLPG prOF7 + (Q32R, C88R, C195R)
                                              (SEQ ID NO: 13)
MSRLDKSKVINSALELLNEVGIEGLTTRKLARKLGVEQPTLYWHVKN
KRALLDALAIEMLDRHHTHFCPLEGESWQDFLRNNAKSFRRALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAAGT
PADALDDFDLDMLPADALDDFDLDMLPADALDDFDLDMLPG prOF7 + (Q32R, C88R, A118R, C195R)
                                              (SEQ ID NO: 14)
MSRLDKSKVINSALELLNEVGIEGLTTRKLARKLGVEQPTLYWHVKN
KRALLDALAIEMLDRHHTHFCPLEGESWQDFLRNNAKSFRRALLSHR
DGAKVHLGTRPTEKQYETLENQLRFLCQQGFSLENALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAAGT
PADALDDFDLDMLPADALDDFDLDMLPADALDDFDLDMLPG
```

-continued prOF14 = prOF7 + (Q32R, C88R, A118R, E128R, C195R)

(SEQ ID NO: 2)

MSRLDKSKVINSALELLNEVGIEGLTTRKLARKLGVEQPTLYWHVKN
KRALLDALAIEMLDRHHTHFCPLEGESWQDFLRNNAKSFRRALLSHR
DGAKVHLGTRPTEKQYETLENQLRFLCQQGFSLRNALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAGT
*PADALDDFDLDMLPADALDDFDLDMLPADALDDFDLDMLPG* prOF14 (-E128R)

(SEQ ID NO: 15)

MSRLDKSKVINSALELLNEVGIEGLTTRKLARKLGVEQPTLYWHVKN
KRALLDALAIEMLDRHHTHFCPLEGESWQDFLRNNAKSFRRALLSHR
DGAKVHLGTRPTEKQYETLENQLRFLCQQGFSLENALYALSAVGHFT
LGCVLEDQEHQVAKEERETPTTDSMPPLLRQAIELFDHQGAEPAFLF
GLELIIRGLEKQLKCESGGPKLHNHNHNHNHNHNEFAAAAAAAAGT
*PADALDDFDLDMLPADALDDFDLDMLPADALDDFDLDMLPG* prOF12

(SEQ ID NO: 16)

MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIICGLEKQLKCESGG*PADALDDFDLDMLPADALDDFDLDMLPA
DALDDFDLDMLPG* prOF12 (+E128R)

(SEQ ID NO: 17)

MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLRNALYALSAVGHFT
LGCVLEDQEHQVAKEERETPTTDSMPPLLRQAIELFDHQGAEPAFLF
GLELIICGLEKQLKCESGG*PADALDDFDLDMLPADALDDFDLDMLPA
DALDDFDLDMLPG* prOF16

(SEQ ID NO: 18)

MSRLDKSKVINSALELLNEVGIEGLTTRKLAQKLGVEQPTLYWHVKN
KRALLDALAIEMLDRHHTHFCPLEGESWQDFLRNNAKSFRCALLSHR
DGAKVHLGTRPTEKQYETLENQLAFLCQQGFSLENALYALSAVGHFT
LGCVLEDQEHQVAKEERETPTTDSMPPLLRQAIELFDHQGAEPAFLF
GLELIICGLEKQLKCESGGPKLHNHNHNHNHNHNEFAAAAAAAAGT
GASMQKLISEEDLGYPYDVPDYAGDYKDDDDK

Figure 3:
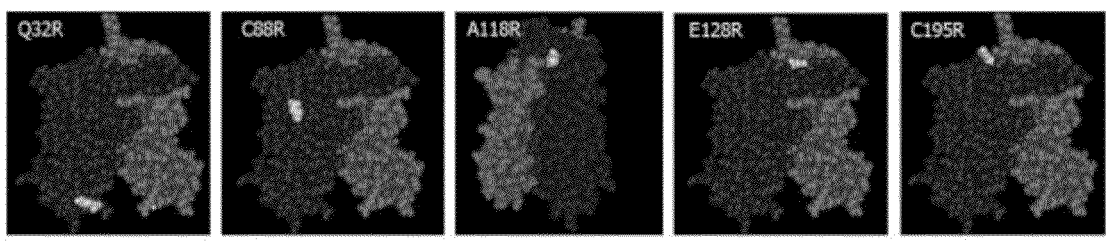
FIG. 3: Mapping the location of the prOF14 mutants in the 3D TetR structure. A prototypical structure of TetR (PDB#2NS7) is shown with the two subunits of the heterodimer colored in pink and blue. The approximate locations of the mutations are indicated in yellow.

The mutated proteins were purified and screened for transactivating activity as before. The best candidate from this screen was a construct called 090827#11 which contained five mutations (Q32R, C88R, A118R, E128R, C195R). This data is summarized in FIGS. 2, 3 & 4. The resultant protein has been named prOF14 and then renamed Tet Express.

Example 2

Use of DNA Transfection Reagents Enhances Transduction

During the development of the Tet Express protein, we noticed that co-addition of several different DNA transfection reagents greatly enhanced the luciferase activity in a Tet reporter cell line. During the course of Tet Express development, we switched from transient transfection of a reporter plasmid to using a stable reporter cell line. These cells are a HeLa based cell line with a stably integrated reporter that expresses ZsGreen1 and firefly luciferase under the control of a TRE-tight promoter (Clontech Laboratories, Mountain View, Calif.). This meant that we no longer needed to do DNA transfection to assay Tet Express activity. We noticed that this switch reduced the observed Tet Express activity and determined that activity could be restored by performing the transduction in the presence of certain DNA transfection reagents. The reagents that enhanced transduction best include Clontech's Xfect, Life Technologies Lipofectamine LTX and 2000 as well as Mirus' SiQuest reagent (FIGS. 5 & 6).

Figure 5:
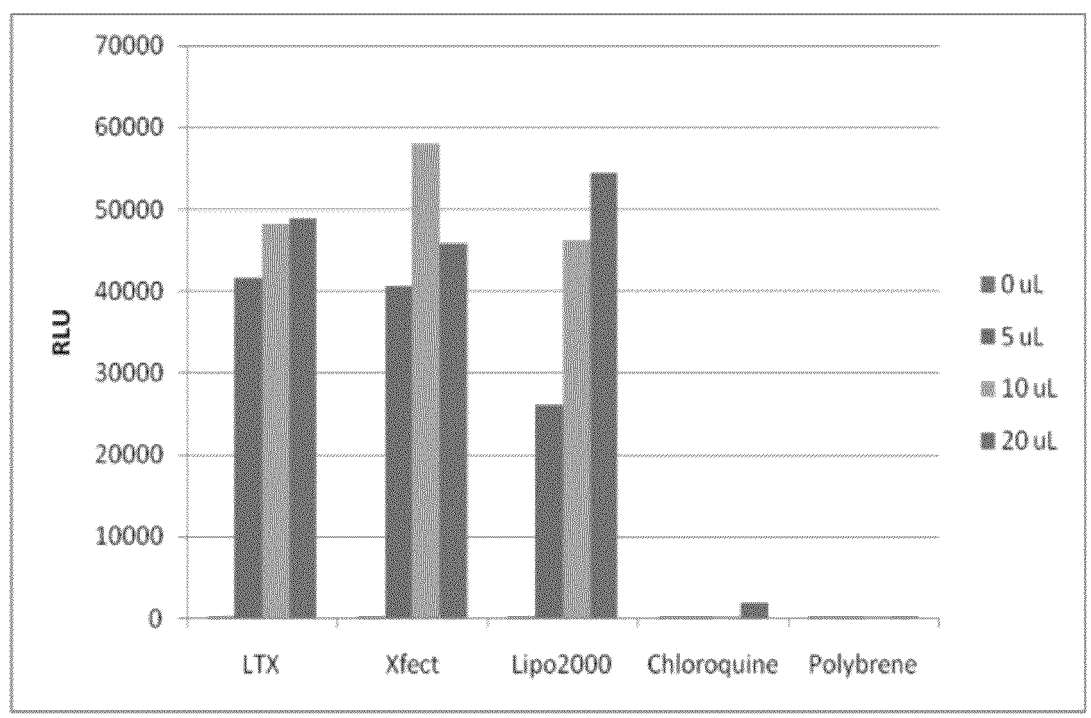
FIG. 5 provides the results of a luciferase assay showing enhancement of Tet Express activity. HeLa reporter cells (Clone 19) with a stable bidirectional TREtight ZsGreen/FLuc integration cassette were plated in 96 well format (15,000 cells per well). After cell attachment, 0, 5, 10 or 20 µL of transduction mix were added per well. Transduction mixes consisted of Tet Express protein in Optimem media with one of the following additions: 2% LTX, 0.6% Xfect, 2% Lipofectamine 2000 (Lipo2000), 0.2 mM chloroquine or 6 µg/mL polybrene. Luciferase assays were performed the following day.

FIG. 5 provides the results of a luciferase assay showing enhancement of Tet Express activity. HeLa reporter cells (Clone 19) with a stable bidirectional TREtight ZsGreen/FLuc integration cassette were plated in 96 well format (15,000 cells per well). After cell attachment, 0, 5, 10 or 20 μL of transduction mix were added per well. Transduction mixes consisted of Tet Express protein in Optimem media with one of the following additions: 2% LTX, 0.6% Xfect, 2% Lipofectamine 2000 (Lipo2000), 0.2 mM chloroquine or 6 μg/mL polybrene. Luciferase assays were performed the following day.

Figure 6:
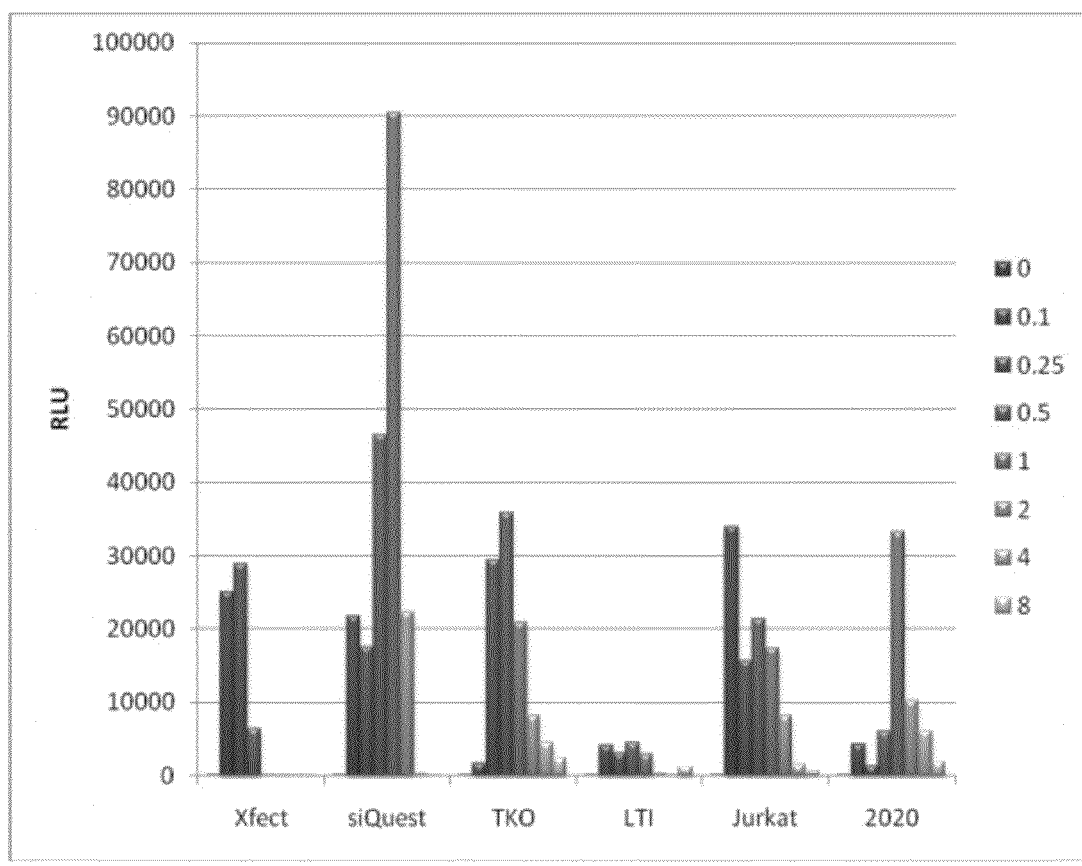
FIG. 6 provides the results of a luciferase assay showing enhancement of Tet Express activity. Clone 19 HeLa reporter cells were plated in 96 well format (15,000 cells per well). Tet Express protein (in Optimem media) was mixed with indicated amount of reagent and added to the cells. Reagents included Mirus' Transit-siQuest, Transit-TKO, Transit-LTI, Transit-Jurkat, Transit-2020 or Clontech's Xfect. Luciferase assays were performed the following day.

FIG. 6 provides the results of a luciferase assay showing enhancement of Tet Express activity. Clone 19 HeLa reporter cells were plated in 96 well format (15,000 cells per well). Tet Express protein (in Optimem media) was mixed with indicated amount of reagent and added to the cells. Reagents included Mirus' Transit-siQuest, Transit-TKO, Transit-LTI, Transit-Jurkat, Transit-2020 or Clontech's Xfect. Luciferase assays were performed the following day.

Other reagents that did show the enhancement effect but to a lesser degree include Mirus' TKO, LTI, Jurkat, & 2020 reagents, chloroquine, PEG. Other reagents which performed poorly, if at all, included, polybrene & DMSO.

Figure 7A:
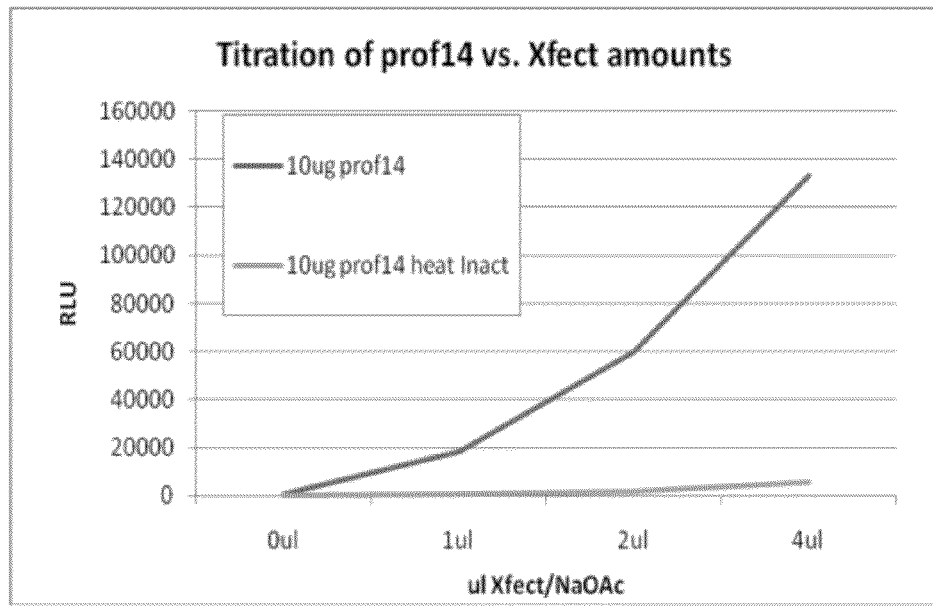
FIG. 7A provides the results of a luciferase assay using heat inactivated Tet Express. Clone 19 HeLa reporter cells were plated in 96 well format (15,000 cells per well). Ten micrograms of Tet Express (prOF14) or heat inactivated Tet Express (75° C. for 5 minutes) was mixed with either: 0, 1, 2 or 4 µL of Xfect and added to the cells. Luciferase assays were performed the following day.
Figure 7B:
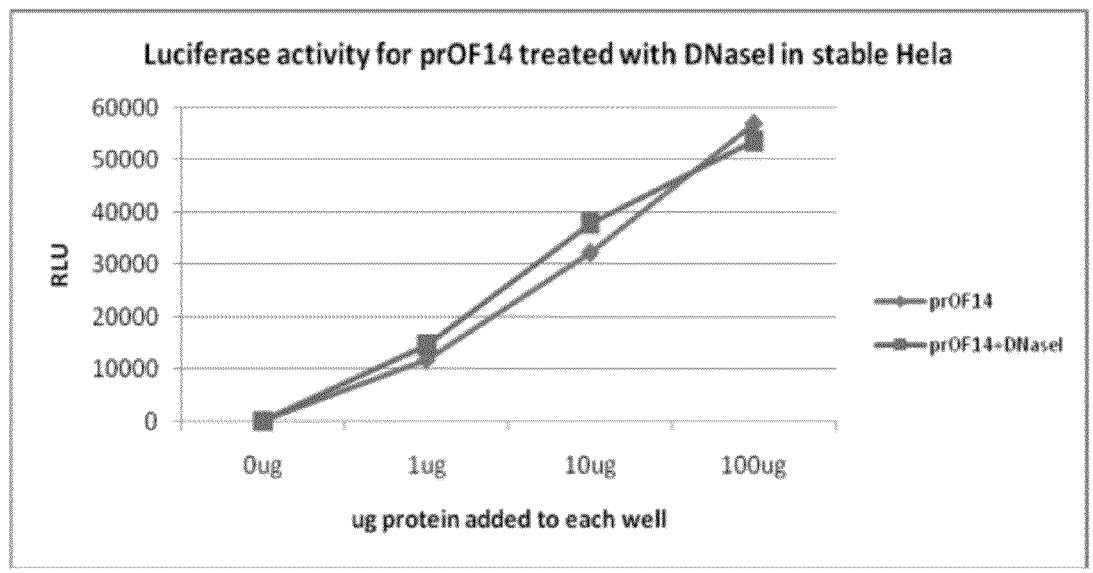
FIG. 7B illustrates that DNase treatment does not alter Tet Express activity. Clone 19 HeLa reporter cells were plated in 96 well format (15,000 cells per well). Tet Express without or with DNase I pretreatment (10 units per 150 µL Tet Express, 37° C. for 30 minutes) was mixed with Xfect and added to cells. Luciferase assay was performed the following day.
Figure 7C:
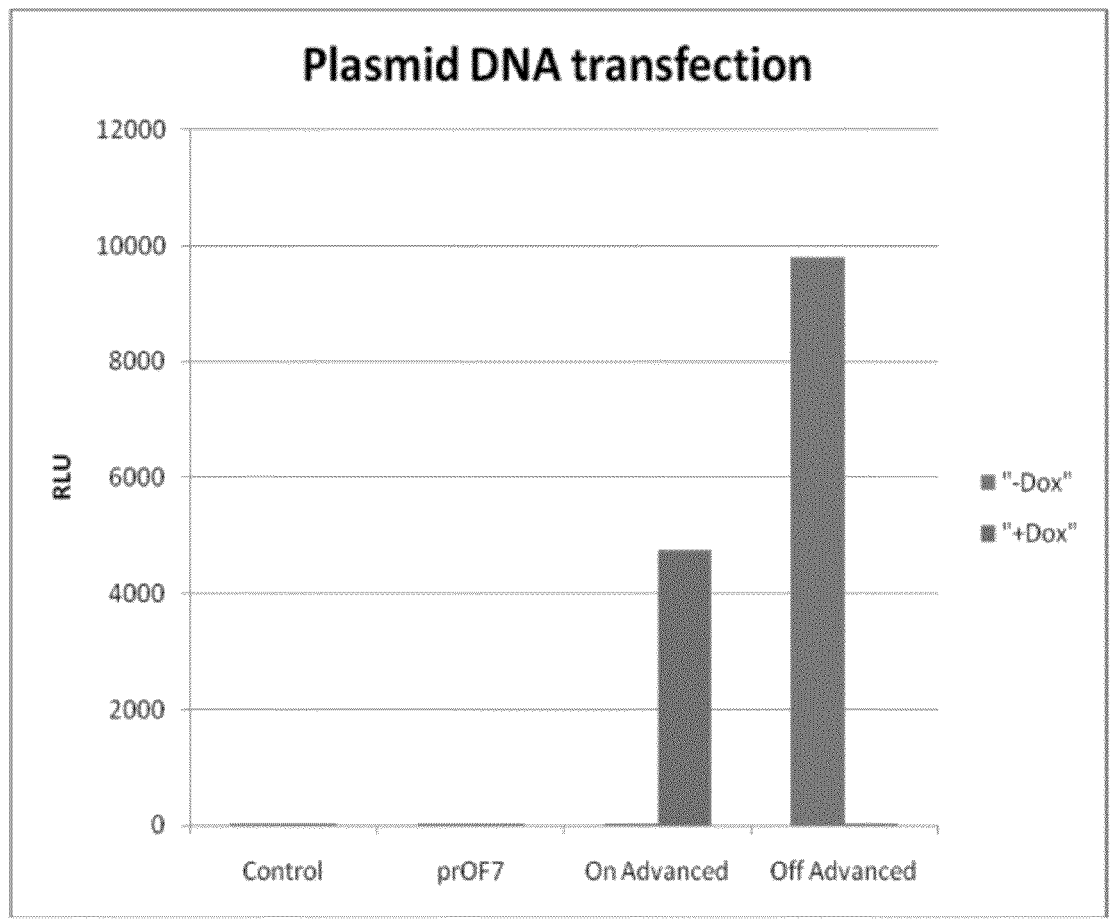
In FIG. 7C., Clone 19 HeLa reporter cells were plated in 12 well format (50,000 cells per well). Cells were transfected with 0.5 µg of pUC19 (control), prOF7, pTet On Advanced or pTet Off Advanced plasmids with 2 µL of Lipofectamine LTX. The following day doxycyline was added to 1000 ng/mL. Luciferase assays were performed the following day.

FIG. 7A provides the results of a luciferase assay using heat inactivated Tet Express. Clone 19 HeLa reporter cells were plated in 96 well format (15,000 cells per well). Ten micrograms of Tet Express or heat inactivated Tet Express (75° C. for 5 minutes) was mixed with either: 0, 1, 2 or 4 μL of Xfect and added to the cells. Luciferase assays were performed the following day. As illustrated in FIG. 7B, DNase treatment does not alter Tet Express activity. Clone 19 HeLa reporter cells were plated in 96 well format (15,000 cells per well). Tet Express without or with DNase I pretreatment (10 units per 150 μL Tet Express, 37° C. for 30 minutes) was mixed with Xfect and added to cells. Luciferase assay was performed the following day. In FIG. 7C., clone 19 HeLa reporter cells were plated in 12 well format (50,000 cells per well). Cells were transfected with 0.5 μg of pUC19 (control), prOF7, pTet On Advanced or pTet Off Advanced plasmids with 2 μL of Lipofectamine LTX. The following day doxycyline was added to 1000 ng/mL. Luciferase assays were performed the following day.

As shown in FIGS. 7A-7C, we addressed the concern that the observed increase in luciferase activity could be due to a contaminating plasmid DNA (i.e., the bacterial expression vector for Tet Express) rather than by enhanced protein transduction. The experiments performed included:

1. Treating the Tet Express protein prep with DNase (had no effect);
2. Heat inactivating the protein prep 5 minutes at 70-75° C. (led to loss of activity);
3. Direct transfection of the bacterial expression vector encoding Tet Express into the mammalian reporter cells (no effect). The results of these experiments ruled out plasmid DNA contamination as the cause of the increased luciferase activity.

Figure 8:
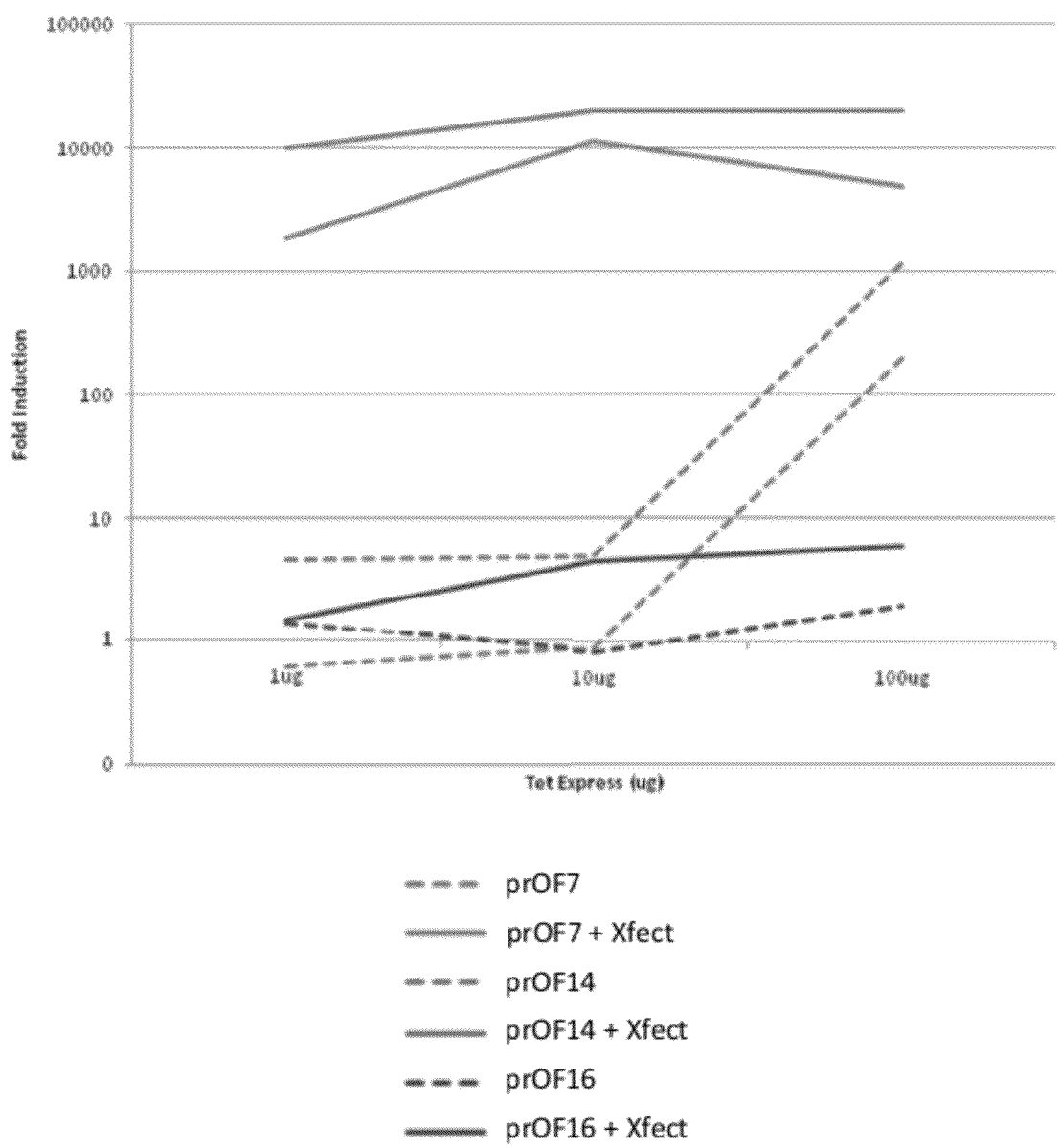
FIG. 8 illustrates the effect of Xfect on Transactivation. Clone 19 HeLa reporter cells were plated at 50,000 cells per well in a 12 well format. Cells were treated with 0, 1, 10 or 100 µg of Tet Express (or derivative) in the presence or absence of Xfect reagent. Luciferase assays were performed the following day.

FIG. 8 illustrates the effect of Xfect (Clontech Laboratories, Mountain View Calif.) on Transactivation. Clone 19 HeLa reporter cells were plated at 50,000 cells per well in a 12 well format. Cells were treated with 0, 1, 10 or 100 μg of Tet Express (or derivative) in the presence or absence of Xfect reagent. Luciferase assays were performed the following day.

Figure 9:
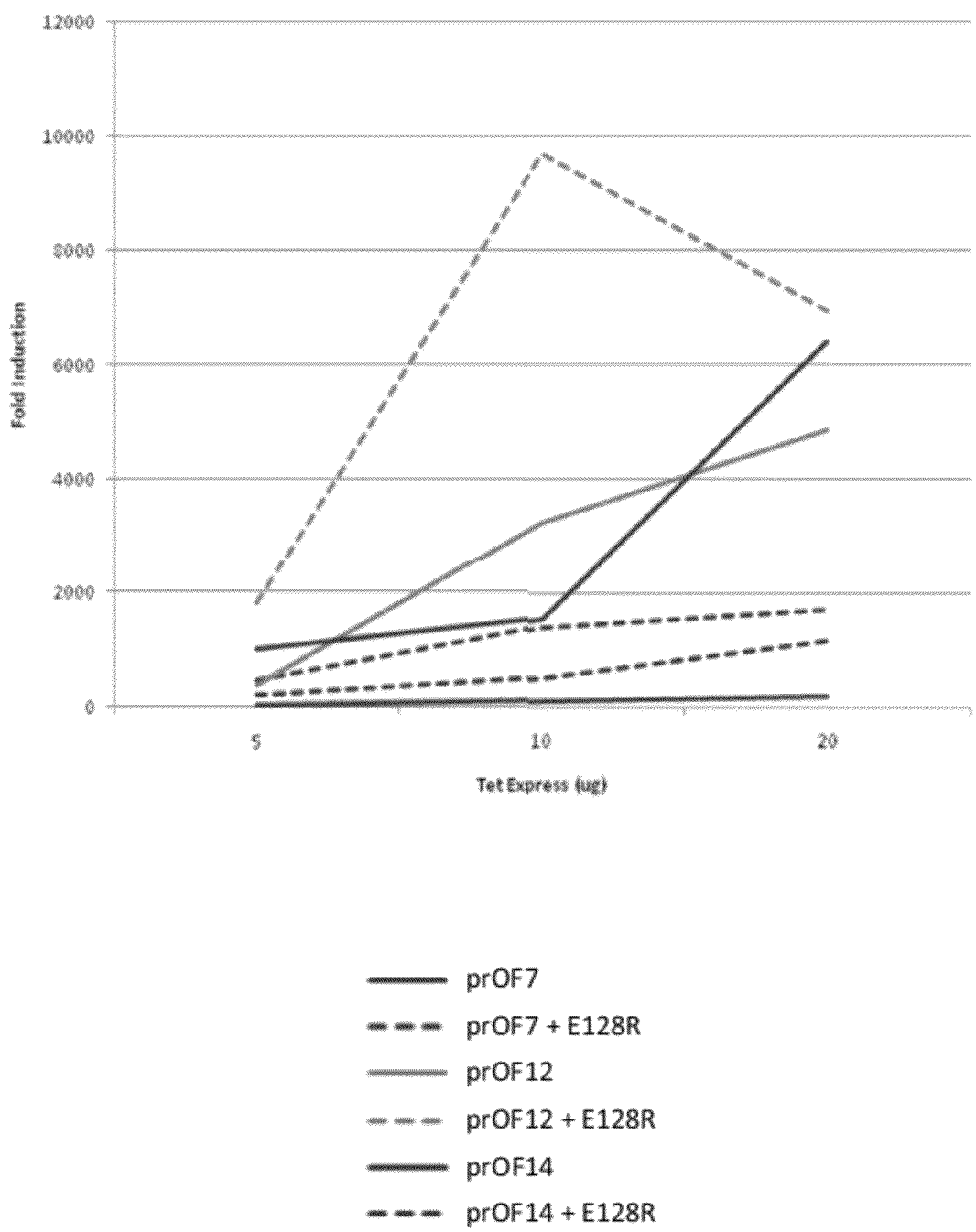
FIG. 9 illustrates the effect of the E128R mutation on PTD activity. Clone 19 HeLa reporter cells were plated at 50,000 cells per well in a 12 well format. Cells were treated with 0, 5, 10 or 20 µg of Tet Express (or derivative) per well in the presence of Mirus Transit-SiQuest reagent (1 µL per well). Luciferase assays were performed the following day.

FIG. 9 illustrates the effect of the E128R mutation. Clone 19 HeLa reporter cells were plated at 50,000 cells per well in a 12 well format. Cells were treated with 0, 5, 10 or 20 μg of Tet Express (or derivative) per well in the presence of Mirus Transit-SiQuest reagent (1 μL per well). Luciferase assays were performed the following day.

Figure 10:
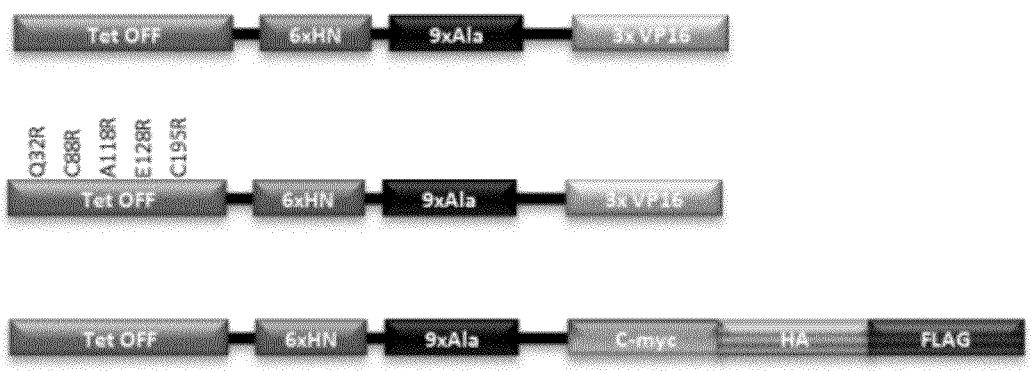
FIG. 10 is a schematic showing the general structure of the prOF7, 14 and 16 proteins. The molecular weight (Mw), number of amino acid residues (#aa) and the isoelectric point (Iso Pt) of each prOF protein is indicated in the chart.

FIG. 10 provides a schematic showing the general structure of the prOF7, 14 and 16 proteins (the diagram is not to scale). The molecular weight (Mw), number of amino acid residues (#aa) and the isoelectric point (Iso Pt) of each prOF protein is indicated in the chart.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An inducible expression system comprising:
   (a) a host cell comprising an expression cassette comprising:
      (i) a transcription modulator responsive element;
      (ii) a promoter; and
      (iii) a coding sequence; and
   (b) a transcription modulator comprising:
      (i) a Tet transcription modulator domain that binds to the transcription modulator responsive element;
      (ii) an expression modulatory domain operably linked to the Tet transcription modulator domain; and
      (iii) a distributed protein transduction domain comprising amino acids that are distributed throughout the Tet transcription modulator domain;
      wherein the transcription modulator comprises one or more point mutations selected from the group consisting of: Q32R, C88R, A118R, E128R, C195R, Q32K, C88K, A118K, E128K, and C195K as compared to Tet Off Advanced protein (SEQ ID NO:4).

2. The expression system according to claim 1, wherein the transcription modulator responsive element is a Tet responsive element.

3. The expression system according to claim 1, wherein the Tet transcription modulator binds to the transcription modulator responsive element in the absence of an expression mediator.

4. The expression system according to claim 1, wherein the Tet transcription modulator binds to the transcription modulator responsive element in the presence of an expression mediator.

5. The expression system according to claim 1, wherein the system further includes an expression mediator.

6. The expression system according to claim 5, wherein the expression mediator is selected from the group consisting of tetracycline and doxycycline.

7. The expression system according to claim 1, wherein the distributed protein transduction domain comprises a basic patch made up 3 or more non-sequential basic amino acid residues.

8. The expression system according to claim 7, wherein the number percentage of basic amino acid residues in the basic patch is 30 or more.

9. The expression system according to claim 1, wherein the expression system further comprises a transduction enhancer.

10. The expression system according to claim 9, wherein the transduction enhancer is a DNA transfection reagent.

11. A transcription modulator comprising:
   (i) a Tet transcription modulator domain that binds to a transcription modulator responsive element;
   (ii) an expression modulatory domain fused to the Tet transcription modulator domain; and
   (iii) a distributed protein transduction domain comprising amino acids that are distributed throughout the Tet transcription modulator domain;
   wherein the transcription modulator comprises one or more point mutations selected from the group consisting of: Q32R, C88R, A118R, E128R, C195R, Q32K, C88K, A118K, E128K, and C195K as compared to Tet Off Advanced protein (SEQ ID NO:4).

12. The Tet transcription modulator domain according to claim 11, wherein the transcription modulator binds to a transcription modulator responsive element in the presence of an expression mediator.

13. The transcription modulator according to claim 11, wherein the transcription modulator binds to a transcription modulator responsive element in the absence of an expression mediator.

14. The transcription modulator according to claim 11, wherein the transcription modulator comprises the following point mutations: Q32R, C88R, A118R, E128R, and C195R.

15. A nucleic acid encoding a transcription modulator comprising:
   (i) a Tet transcription modulator domain that binds to a transcription modulator responsive element;
   (ii) an expression modulatory domain fused to the transcription modulator domain; and
   (iii) a distributed protein transduction domain comprising amino acids that are distributed throughout the Tet transcription modulator domain;
   wherein the transcription modulator comprises one or more point mutations selected from the group consisting of: Q32R, C88R, A118R, E128R, C195R, Q32K, C88K, A118K, E128K, and C195K as compared to Tet Off Advanced protein (SEQ ID NO:4).

16. The nucleic acid according to claim 15, wherein the transcription modulator comprises the following point mutations: Q32R, C88R, A118R, E128R, and C195R.

17. The nucleic acid according to claim 15, wherein the nucleic acid is present in a vector.

18. The nucleic acid according to claim 15, wherein the nucleic acid is present in a cell.

19. A method of inducing expression of a coding sequence in a host cell, the method comprising:
   (a) providing a host cell comprising:
     (i) an expression cassette comprising: a transcription modulator responsive element, a promoter and the coding sequence; and
     (ii) a transcription modulator comprising: a Tet transcription modulator domain that binds to the transcription modulator responsive element in an expression mediator mediated manner, an expression modulatory domain operably linked to the Tet transcription modulator domain, and a distributed protein transduction domain comprising amino acids that are distributed throughout the Tet transcription modular domain, wherein the transcription modulator comprises one or more point mutations selected from the group consisting of: Q32R, C88R, A118R, E128R, C195R, Q32K, C88K, A118K, E128K, and C195K as compared to Tet Off Advanced protein (SEQ ID NO:4); and
   (b) maintaining the host cell under conditions sufficient to induce expression of the coding sequence.

20. A kit comprising:
   a) a vector comprising an expression cassette comprising:
     (i) a transcription modulator responsive element;
     (ii) a promoter; and
     (iii) a cloning site; and
   (b) a transcription modulator comprising:
     (i) a Tet transcription modulator domain that binds to the regulatory protein responsive element;
     (ii) an expression modulatory domain operably linked to the Tet transcription modulator domain; and
     (iii) a distributed protein transduction domain comprising amino acids that are distributed throughout the Tet transcription modular domain, wherein the transcription modulator comprises one or more point mutations selected from the group consisting of: Q32R, C88R, A118R, E128R, C195R, Q32K, C88K, A118K, E128K, and C195K as compared to Tet Off Advanced protein (SEQ ID NO:4).

21. The expression system according to claim 1, wherein the distributed protein transduction domain comprises non-sequential amino acid residues separated in primary sequence by one or more intervening residues.

* * * * *

UNITED STATES PATENT AND TRADEMARK OFFICE
CERTIFICATE OF CORRECTION

| | |
|---|---|
| PATENT NO. | : 9,127,283 B2 |
| APPLICATION NO. | : 13/303652 |
| DATED | : September 8, 2015 |
| INVENTOR(S) | : Bisgrove et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 78 days.

In the Drawings:

Sheet 10, Fig. 9, in the legend the last series label "prOF14 + E128" should read -- prOF14 – E128R --.

Signed and Sealed this
Fifth Day of April, 2016

Michelle K. Lee
*Director of the United States Patent and Trademark Office*